(12) United States Patent
Ragland

(10) Patent No.: US 6,847,900 B2
(45) Date of Patent: Jan. 25, 2005

(54) SYSTEM AND METHOD FOR IDENTIFYING SOLDER JOINT DEFECTS

(75) Inventor: Tracy Kristine Ragland, Boulder, CO (US)

(73) Assignee: Agilent Technologies, Inc., Palo Alto, CA (US)

(*) Notice: Subject to any disclaimer, the term of this patent is extended or adjusted under 35 U.S.C. 154(b) by 106 days.

(21) Appl. No.: 10/024,101

(22) Filed: Dec. 17, 2001

(65) Prior Publication Data

US 2003/0114996 A1 Jun. 19, 2003

(51) Int. Cl.⁷ .............................................. G06F 19/00
(52) U.S. Cl. .......................................... 702/35; 378/58
(58) Field of Search ....................... 702/35, 33; 378/58; 356/237.1; 250/559.22, 341.6; 382/147

(56) References Cited

U.S. PATENT DOCUMENTS

| | | | |
|---|---|---|---|
| 4,792,683 A | * 12/1988 | Chang et al. | ............ 250/341.6 |
| 4,926,452 A | 5/1990 | Baker et al. | .................. 378/22 |
| 5,081,656 A | 1/1992 | Baker et al. | .................. 378/21 |
| 5,097,492 A | 3/1992 | Baker et al. | .................. 378/22 |
| 5,199,054 A | 3/1993 | Adams et al. | ................. 378/21 |
| 5,259,012 A | 11/1993 | Baker et al. | .................. 378/21 |
| 5,291,535 A | 3/1994 | Baker et al. | .................. 378/22 |
| 5,561,696 A | 10/1996 | Adams et al. | ................. 378/58 |
| 5,583,904 A | 12/1996 | Adams | ........................ 378/22 |
| RE35,423 E | * 1/1997 | Adams et al. | ................. 378/58 |
| 5,621,811 A | 4/1997 | Roder et al. | ................ 382/147 |
| 5,687,209 A | 11/1997 | Adams | ........................ 378/22 |
| 5,780,866 A | * 7/1998 | Yamamura et al. | .... 250/559.22 |
| 6,580,501 B2 | * 6/2003 | Cannon | ................... 356/237.1 |

* cited by examiner

*Primary Examiner*—John Barlow
*Assistant Examiner*—Xiuqin Sun

(57) ABSTRACT

An improved circuit inspection system incorporates an automated measuring technique that accounts for acceptable Z-axis elevation variance across both a printed-circuit device and a mounting surface when making solder-joint pass/fail decisions. The improved solder-joint inspection system applies a near neighbor solder joint diameter error analysis for each solder joint on a printed-circuit device. A near neighbor solder joint diameter error outlier analysis is used to identify solder joint defects with improved accuracy.

44 Claims, 15 Drawing Sheets

SYSTEM AND METHOD FOR IDENTIFYING SOLDER JOINT DEFECTS

TECHNICAL FIELD

The present disclosure relates generally to systems and methods for high-resolution inspection of circuit board assemblies using measurement systems, and in particular, to systems which measure solder joints within circuit board assemblies for quality control analysis.

BACKGROUND OF THE INVENTION

Rapid and precise quality control inspections of the soldering and assembly of electronic devices have become priority items in the electronics manufacturing industry. The reduced size of components and solder connections, the resulting increased density of components on circuit board assemblies and the advent of surface mount technology (SMT), which places solder connections underneath device packages where they are hidden from view, have made rapid and precise inspections of electronic devices and the electrical connections between devices very difficult to perform in a manufacturing environment.

Many existing inspection systems for electronic devices and connections make use of penetrating radiation to form images, which exhibit features representative of the internal structure of the devices and connections. These systems often utilize conventional radiographic techniques wherein the penetrating radiation comprises X-rays. Medical X-ray pictures of various parts of the human body, e.g., the chest, arms, legs, spine, etc., are perhaps the most familiar examples of conventional radiographic images. The images or pictures formed represent the X-ray shadow cast by an object being inspected when it is illuminated by a beam of X-rays. The X-ray shadow is recorded by an X-ray sensitive material such as film or other suitable means.

The appearance of the X-ray shadow or radiograph is determined not only by the internal structural characteristics of the object, but also by the direction from which the incident X-rays strike the object. Therefore, a complete interpretation and analysis of X-ray shadow images, whether performed visually by a person or numerically by a computer, often requires that certain assumptions be made regarding the characteristics of the object and its orientation with respect to the X-ray beam. For example, it is often necessary to make specific assumptions regarding the shape, internal structure, etc. of the object and the direction of the incident X-rays upon the object. Based on these assumptions, features of the X-ray image may be analyzed to determine the location, size, shape, etc., of the corresponding structural characteristic of the object, e.g., a defect in a solder connection, which produced the image feature. These assumptions often create ambiguities, which degrade the reliability of the interpretation of the images and the decisions based upon the analysis of the X-ray shadow images. One of the primary ambiguities resulting from the use of such assumptions in the analysis of conventional radiographs is that small variations of a structural characteristic within an object, such as the shape, density, and size of a defect within a solder connection, are often masked by the overshadowing mass of the solder connection itself as well as by solder connections on the opposite side of the circuit board, electronic devices, circuit boards, and other objects. Since the overshadowing mass is usually different for each solder joint, it is extremely cumbersome and often nearly impossible to make enough assumptions to precisely determine shapes, sizes, and locations of solder defects within individual solder joints.

In an attempt to compensate for such shortcomings, some systems incorporate the capability of viewing the object from a plurality of angles. The additional views enable these systems to partially resolve the ambiguities present in the X-ray shadow projection images. However, utilization of multiple viewing angles necessitates a complicated mechanical handling system, often requiring as many as five independent, non-orthogonal axes of motion. This degree of mechanical complication leads to increased expense, increased size and weight, longer inspection times, reduced throughput, impaired positioning precision due to the mechanical complications, and calibration and computer control complications due to the non-orthogonality of the axes of motion.

Many of the problems associated with the conventional radiography techniques discussed above may be alleviated by producing cross-sectional images of the object being inspected. Tomographic techniques such as laminography and computer-aided tomography (CT) have been used in medical applications to produce cross-sectional or body-section images. In medical applications, these techniques have met with widespread success, largely because relatively low resolution on the order of one or two millimeters (approximately 0.04 to 0.08 inches) is satisfactory and because speed and throughput requirements are not as severe as the corresponding industrial requirements.

In the case of electronics inspection, and more particularly, for inspection of electrical connections such as solder joints, image resolution on the order of several micrometers, for example, 20 micrometers (approximately 0.0008 inches) is preferred. Furthermore, an industrial solder-joint inspection system must generate multiple images per second in order to be of practical use on an industrial production line.

Laminography systems which are capable of achieving the speed and accuracy requirements necessary for electronics inspection are described in the following patents: U.S. Pat. No. 4,926,452, entitled, "AUTOMATED LAMINOGRAPHY SYSTEM FOR INSPECTION OF ELECTRONICS," issued to Baker et al.; U.S. Pat. No. 5,097,492, entitled, "AUTOMATED LAMINOGRAPHY SYSTEM FOR INSPECTION OF ELECTRONICS," issued to Baker et al.; U.S. Pat. No. 5,081,656, entitled, "AUTOMATED LAMINOGRAPHY SYSTEM FOR INSPECTION OF ELECTRONICS," issued to Baker et al.; U.S. Pat. No. 5,291,535, entitled, "METHOD AND APPARATUS FOR DETECTING EXCESS/INSUFFICIENT SOLDER DEFECTS," issued to Baker et al.; U.S. Pat. No. 5,621,811, entitled, "LEARNING METHOD AND APPARATUS FOR DETECTING AND CONTROLLING SOLDER DEFECTS," issued to Roder et al.; U.S. Pat. No. 5,561,696, entitled, "METHOD & APPARATUS FOR INSPECTING ELECTRICAL CONNECTIONS," issued to Adams et al.; U.S. Pat. No. 5,199,054, entitled, "METHOD AND APPARATUS FOR HIGH RESOLUTION INSPECTION OF ELECTRONIC ITEMS," issued to Adams et al.; U.S. Pat. No. 5,259,012, entitled, "LAMINOGRAPHY SYSTEM AND METHOD WITH ELECTROMAGNETICALLY DIRECTED MULTIPATH RADIATION SOURCE," issued to Baker et al.; U.S. Pat. No. 5,583,904, entitled, "CONTINUOUS LINEAR SCAN LAMINOGRAPHY SYSTEM AND METHOD," issued to Adams; and U.S. Pat. No. 5,687,209, entitled, "AUTOMATIC WARP COMPENSATION FOR LAMINOGRAPHIC CIRCUIT BOARD INSPECTION," issued to Adams. The entirety of each of the above referenced patents is hereby incorporated herein by reference.

In a laminography system, which views a fixed object and has an imaging area that is smaller than the object being inspected, it may be necessary to move the object around to position different regions of the object within the imaging area thus generating multiple laminographs, which when pieced together form an image of the entire object. This is frequently achieved by supporting the object on a mechanical handling system, such as an X-Y-Z positioning table. The table is then moved to bring the desired regions of the object into the imaging area. Movement in the X and Y directions locates the region to be examined, while movement in the Z direction moves the object up and down to select the plane within the object where the cross-sectional image is taken.

Several of the above-referenced patents disclose devices and methods for the generation of cross-sectional images of test objects at a fixed or selectable cross-sectional image focal plane. In these systems, an X-ray source system and an X-Ray detector system are separated in the "Z" axis direction by a fixed distance and the cross-sectional image focal plane is located at a predetermined specific position in the "Z" axis direction which is intermediate the positions of the X-ray source system and the X-ray detector system along the "Z" axis. The X-Ray detector system collects data from which a cross-sectional image of features in the test object, located at the cross-sectional image focal plane, can be formed. These systems postulate that the features desired to be imaged are located in the fixed or selectable cross-sectional image focal plane at the predetermined specific position along the "Z" axis. Thus, in these systems, it is essential that the positions of the cross-sectional image focal plane and the plane within the object, which is desired to be imaged, be configured to coincide at the same position along the "Z" axis. If this condition is not met, then the desired image of the selected feature within the test object will not be acquired. Instead, a cross-sectional image of a plane within the test object, which is either above or below the plane that includes the selected feature will be acquired. In some arrangements, less than optimal views of a solder joint may be imaged. Consequently, analysis of these less than optimal views can lead to inaccurate analysis of the associated solder-joint.

Presently, one technique commonly used for positioning the selected feature of the test object within the cross-sectional image focal plane, physically measures the "Z"-axis position of the selected feature. Using this measurement, the test object is then positioned along the "Z" axis such that the selected feature coincides with the "Z"-axis position of the cross-sectional image focal plane. Any of a variety of standard methods and instruments may be used to physically measure the "Z"-axis position of the selected feature of the test object. There are several types of commercially-available Z-ranging systems, which are used to determine the distance between a known location in "Z" and a feature on the surface, or just below the surface, of the test object. Such systems may be as simple as a mechanical fixing of the test object, a mechanical probe, a laser-based optical triangulation system, an optical-interferometric system, an ultrasonic system, among others. Any one of these "Z"-axis position measuring systems may be used to form a "Z-map" of the surface of the test object. The "Z-map" typically consists of an array of X and Y positions associated array of the Z-values of the surface of the test object. The locations (i.e., X, Y positions) are points on a plane shared with the test object that is substantially parallel to the cross-sectional image focal plane. The systems most commonly used in systems for cross-sectional image features on printed-circuit boards are laser-based triangulation range finders.

Range finders have been used in particular for cross-sectional X-ray image systems that are used to image electronic circuit board assemblies. Circuit-board assemblies are typically very thin in comparison to the surface area in which the components are mounted. Some circuit assemblies are made with very dimensionally-stable material, such as ceramic substrates. However, the majority of circuit-board assemblies are constructed with a material that is somewhat flexible or in some cases very flexible. This flexibility allows the board to develop a warp in the axis perpendicular to the major surface areas (i.e., the surface areas that contain interface pins) or the "Z" dimension. Additionally, some circuit board assemblies have variations in board thickness. In addition to electronic assemblies, there are many other objects that have dimensional variation on a scale that is significant when compared to the depth of field of the "Z" focal plane in cross-sectional X-ray imaging. By measuring the surface of a warped test object, the magnitude of the variation in the "Z" dimension can then be used to properly adjust the positional relationship of the test object with respect to the "Z" focal plane of the cross-sectional imaging system so that the desired image of the features of interest within the test object can be imaged.

Specifically, one such range finder system is designed for use in a system such as that described in U.S. Pat. No. 4,926,452 to Baker, et al. Hereafter referred to as the '452 patent. The '452 patent discloses a laminography system in which an X-ray based imaging system having a very shallow depth of field is used to examine solid objects such as printed-circuit boards. The shallow depth of field provides a means for examining the integrity of a solder joint without interference from the components above and below the solder joint. The material above and below the solder joint is out of focus, and hence, contributes to a more or less uniform background. To provide the needed selectivity, the depth of field of the laminographic-imaging system is on the order of less than approximately 2 millionths of an inch (2 mils.). Unfortunately, surface variations on the printed-circuit board often exceed this tolerance. To overcome this drawback, the surface of the printed-circuit board is mapped using a laser-range finder. The detailed laser-range finder generated map is then used to position the circuit board with respect to the X-ray imaging system such that the component of interest is in focus even when the board is translated from one field of interest to another.

One disadvantage of solder-joint inspection systems is the methodology used in determining whether a measured solder-joint feature is indicative of a solder joint that is "acceptable" or "defective." Present solder-joint inspection systems apply a pre-set threshold to each solder joint feature in order to make these determinations. This methodology for identifying "defective" solder joints is problematic for determining when an individual solder joint on an array package is "defective." This is especially evident in the accuracy rate of identified "open circuits" for solder joints associated with various array package types.

Ball-grid array (BGA) circuit packages, for example, have a planar-bottom face or mounting surface that is generally either square or rectangular in shape. This face may be covered with small spherical leads that carry electric signals to and from the integrated circuit that is a part of the "chip" or integrated circuit package. As is known, the planar bottom forms part of a substrate (typically a multi-layered substrate) to which an integrated circuit die is affixed.

A number of factors combine such that there are significant measurable differences from solder ball (i.e., a solder joint) to solder ball across the surface of an array package.

First, the package material may warp resulting in a significant variation in the relative distance between the mounting surfaces of the package and a printed-circuit board. Generally, BGA packages warp such that the edges tend to pull away from the mounting surface of the printed-circuit board (i.e., the edges turn upward). However, it should be appreciated that BGA-package warp can occur in a host of various ways with the distance between the mounting surfaces of a BGA package and a printed-circuit board varying in a number of different ways across the mounting surfaces. Other packages, such as, but not limited to column grid array (CGA), flip-chip, chip scale packages (CSPs), and quad flat packs, etc. may also suffer from warp.

In addition to package warp, the printed-circuit board material may warp. It should be appreciated that these two conditions are not mutually exclusive of each other. Stated in another way, both the printed-circuit board (i.e., a mounting surface) and the package may be warped. Furthermore, either of the printed-circuit board and/or the package may suffer from "tilt." A "tilt" condition is present when the mounting surface elevation (i.e., height in the "Z" dimension) varies from one edge to an opposing edge on either a package or a printed-circuit board.

These and other factors may work together such that a printed-circuit assembly may contain a plurality of multi-pin devices (e.g., array packages) with a significant variation in one or more solder-joint measurements. For example, in the case of substantially uniform (in volume) solder balls applied to the mounting surface conductors of a BGA package, an increase in the distance between the mounting surfaces of the BGA package and the printed-circuit board may cause one or more solder balls to stretch such that its diameter is less than that of the solder ball in its pre-reflow condition. Generally, the solder balls collapse from their pre-reflow condition. The balls closer to the center of the array typically collapse more than the solder balls closer to the external edges of the array.

Despite a wide range of measured solder-joint characteristics across the multitude of connecting pin locations on an array package, the associated conductors on the printed-circuit assembly and the array package may be adequately connected, both structurally and electrically, via the corresponding solder-joint. Any associated differences in the various measurements of the solder-joints (in those situations where corresponding conductors are adequately connected) is representative of an acceptable variation across the plurality of solder-joint measurements.

The wide range of acceptable solder-joint measurements makes it extremely difficult to set pass/fail thresholds for various measurements of solder-joints that accurately reflect the actual electrical and physical condition of each individual solder-joint. In practice, the accurate detection of "open circuit" conditions with solder-joint inspection systems for BGA devices has been problematic. Not only is it time consuming to rework each BGA package identified as having one or more "defective" solder-joint test results, short of a full functional test of the printed-circuit assembly (i.e., a completely populated printed-circuit board), or in-circuit test of the part, which requires 100% electrical test access, no non-destructive verification method exists to independently confirm the accuracy of the defect conclusion.

In response, some manufacturers have used oval shaped pads with various printed-circuit devices. The oval shaped pads cause solder balls to form oval shaped solder joints when the pad is properly bonded by the solder. The oval shaped pads permit detection of "open" solder joints as the associated solder image remains circular. Despite this and other improvements in detecting defective solder joints, it would be desirable to have an improved system and method for improving the accuracy of solder-joint inspection systems in accurately identifying defective solder-joints used to physically and electrically connect various printed-circuit devices on printed-circuit boards that accounts for acceptable variation in measured solder joints on a printed-circuit assembly.

SUMMARY OF THE INVENTION

In response to these and other shortcomings of the prior art, a solder-joint inspection system and method for adapting test thresholds to identify solder-joint defects are disclosed. In one arrangement, the solder-joint inspection system records location information regarding a plurality of pins (i.e., solder-joint interfaces) on each printed-circuit device of a printed-circuit assembly (i.e., a device populated printed-circuit board) as well as information regarding the variation in distance between the mounting surface of the printed-circuit assembly, and device package. The solder-joint inspection system generates an expected pass/fail criteria for each solder joint that accounts for acceptable variation in actual measurement values recorded for the set of solder joints on each printed-circuit device. Briefly described, in architecture, an improved solder-joint inspection system can be realized with a means for measuring a solder joint; a means for computing; and a data storage means.

Some embodiments of the system can be viewed as providing a method for identifying solder joint defects. In this regard, the method can be summarized by the following steps: recording a measurement of each solder joint on a printed-circuit assembly; estimating an expected value for each of the solder joints that accounts for acceptable variance in elevation of the printed-circuit device with respect to a printed-circuit board; comparing the recorded measurement with the expected value for each solder joint to generate a error value for each solder joint; and identifying measurement error outliers.

Other embodiments of the system can be viewed as providing a method for adapting test thresholds. In this regard, the method can be summarized by the following steps: acquiring location information for a plurality of pins on a printed-circuit device; obtaining information indicative of height variation across a mounting surface of the printed-circuit device; recording a measurement of a plurality of solder joints associated with the plurality of pins; estimating a range of acceptable measurements for respective solder joints responsive to the height variation across the mounting surface; and setting at least one threshold responsive to a limit of the range.

Other systems, methods, and features associated with the adaptation of test thresholds that account for acceptable solder joint diameter variance in a printed-circuit assembly will become apparent to one with skill in the art upon examination of the following drawings and detailed description. It is intended that all such additional systems, methods, and features included within this description, are within the scope of the systems and methods for identifying solder joint defects as protected by the accompanying claims.

BRIEF DESCRIPTION OF THE DRAWINGS

The systems and methods for adapting test thresholds for identifying solder joint defects can be better understood with reference to the following drawings. The components in the drawings are not necessarily to scale emphasis instead is placed upon clearly illustrating the principles of the test methods and the adaptation of test thresholds that account for acceptable solder joint measurement variance across a printed-circuit device on a printed-circuit assembly. Furthermore, in the drawings, like reference numerals designate corresponding parts throughout the several views.

DETAILED DESCRIPTION

Figure 1:
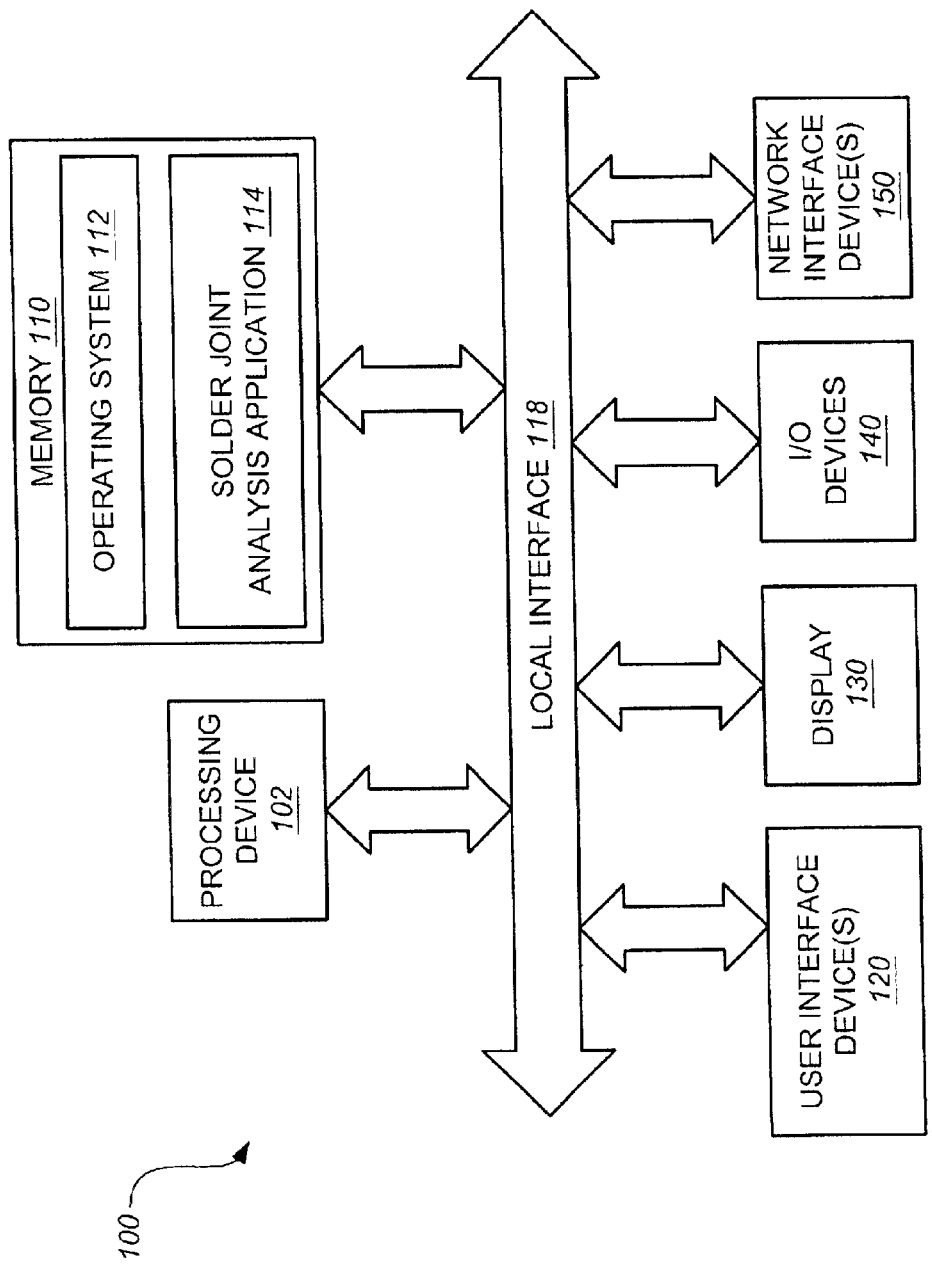
FIG. 1 is a block diagram of an exemplar circuit inspection system.

The present invention is directed to a system and method, which addresses the above listed problems. Particularly important is that an improved solder-joint inspection system configured to apply the method for adapting test thresholds may significantly reduce the number of false "defects" identified upon analyzing one or more measurements of each individual solder joint. An improved solder-joint inspection system configured in accordance with the method for adapting test thresholds accounts for acceptable variation in the distance between the mounting surfaces of a printed-circuit device package and a printed-circuit board when setting pass/fail criteria. More specifically, the method for adapting test thresholds accepts low-frequency variation in measured parameters of adjacent solder joints across the mounting surface of the printed-circuit device, while identifying high-frequency variation between adjacent solder joints.

To facilitate the description of the system and method, an exemplar system is discussed with reference to the figures. The exemplar system and associated methods are provided for purposes of illustration only. Various modifications are feasible without departing from the inventive concept.

For example, the exemplar data, figures, and related description are focused on diameter measurements associated with solder joints affixed to BGA packages. Those skilled in the art will appreciate that low-frequency variation occurs in other solder joint types (i.e., non-spherical joints) at least due to the same reasons that cause BGA packages and printed-circuit boards to warp. Consequently, the method for adapting test thresholds will be applicable to various other solder joint types.

In accordance with preferred embodiments, a commercially-available solder-joint inspection system, such as the 5DX X-ray Inspection System available from Agilent Technologies of Palo Alto, Calif., records location information regarding a plurality of pins (i.e., solder-joint interfaces) on each printed-circuit device of a printed-circuit assembly (i.e., a device populated printed-circuit board). Using the location information, the solder-joint inspection system associates each of the plurality of pins with a set of neighbor pins (i.e., adjacent pins) on each respective printed-circuit device. After recording at least one actual measurement of a characteristic of each solder joint under inspection, the solder-joint inspection system generates an expected pass/fail criteria for each measurement associated with each respective solder joint that accounts for acceptable (i.e., low-frequency) variation in the actual measurement values recorded. Exemplar characteristics of a solder joint that may be measured may include thickness, shape, heel height, solder volume, among others.

Several estimating techniques may be used to identify individualized expected values for each pin of a printed-circuit device. For example, one embodiment uses a statistical value derived from a set of adjacent solder joint measurements to estimate an expected measurement of a present solder joint under test. Statistical values may include an average, a mean, a median, etc. In a variation of this first embodiment, measurements recorded from across the mounting surface may be sampled when estimating the expected values. In other words, the estimated values for each solder joint used to couple a 100 pin device could be determined from actual measurements from a subset of solder joints across the 100 pin device.

A second embodiment performs a two-dimensional polynomial fit over the measurement data to identify an expected measurement value for a solder joint under test. A third embodiment employs a Fourier analysis over the measured results to identify high-frequency variations between adjacent solder joints. An inverse Fourier transform can be used to identify an expected measurement value for specific solder joints. Once an expected measurement value is associated with each solder joint of a package under test, the solder-joint inspection system can perform a comparison of the actual measured value for each particular solder joint of interest with the associated expected value to generate an error value. After an error value is associated with respective solder joints under test on each printed-circuit device, an outlier analysis can be performed to derive a custom pass/fail criteria for each solder joint.

Referring now to FIG. 1, illustrated is a functional block diagram showing various components within an exemplar solder-joint inspection system 100. Generally, FIG. 1 is a schematic illustrating the various functional building blocks of a computer-based solder-joint inspection system, which can apply the various methods for identifying solder-joint defects. Generally, the solder-joint inspection system 100 can comprise any one of a wide variety of wired and/or wireless computing devices, such as a desktop computer, a portable computer, a dedicated server computer, a multi-processor computing device, among others. Irrespective of its specific arrangement, the solder-joint inspection system 100 can, for instance, comprise a processing device 102, memory 110, one or more user interface devices 120, a display 130, one or more input/output (I/O) devices 140, and one or more network interface devices 150, each of which is connected via a local interface 118.

The processing device 102 can include any custom made or commercially available processor, a central processing unit (CPU) or an auxiliary processor among several processors associated with the solder-joint inspection system 100, a semiconductor based microprocessor (in the form of a microchip), a macro-processor, one or more application-specific integrated circuits (ASICs), a plurality of suitably configured digital logic gates, and other well known electrical configurations comprising discrete elements both individually and in various combinations to coordinate the overall operation of the solder-joint inspection system 100.

The memory 110 can include any one of a combination of volatile memory elements (e.g., random access memory (RAM, such as DRAM, SRAM, etc.)) and non-volatile memory elements (e.g., ROM, hard drive, tape, CDROM, etc.). The memory 110 typically comprises an O/S 112, one or more applications such as a solder-joint analysis application 114. Persons having ordinary skill in the art will appreciate that the memory 110 can, and typically will, comprise other components, which have been omitted for purposes of brevity. These may include a host of programs configured to control various aspects of the solder-joint inspection mechanisms.

The one or more user interface devices 120 comprise those components with which the user can interact with the solder-joint inspection system 100. For example, where the solder-joint inspection system 100 comprises a personal computer (PC), these components can comprise a keyboard and mouse. Where the solder-joint inspection system 100 is expected to be used in extreme environments (e.g., near a solder flow machine), these components can comprise function keys or buttons, a touch-sensitive screen, a stylus, etc. The display 130 can comprise a computer monitor or plasma screen for a PC or alternatively a liquid crystal display (LCD) as may be desired.

With further reference to FIG. 1, the one or more I/O devices 140 are adapted to facilitate connection of the solder-joint inspection system 100 to another system and/or device and may therefore include one or more serial, parallel, small computer system interface (SCSI), universal serial bus (USB), IEEE 1394 (e.g., Firewire™), and/or other interface components that may be used to communicatively couple the solder-joint inspection system 100 with one or more remote data storage devices for recording test measurement results. The network interface devices 150 comprise the various components used to transmit and/or receive data over a network. By way of example, the network interface devices 150 may include a device that can communicate both inputs and outputs, for instance, a modulator/demodulator (e.g., a modem), wireless (e.g., a radio-frequency (RF)) transceiver, a telephonic interface, a bridge, a router, a network card, etc.

Various software and/or firmware will be used to manage, coordinate, measure, record, estimate and compare expected values with measured values to generate error values, as well as to perform an outlier analysis on the generated error values, among other functions. The related software and/or firmware responsible for theses and other functions associated with the use of the underlying solder-joint inspection system 100 can be stored on any computer-readable medium for use by or in connection with any computer-related system or method. In the context of this document, a computer-readable medium denotes an electronic, magnetic, optical, or other physical device or means that can contain or store a computer program for use by or in connection with a computer-related system or method. These programs can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer-readable medium can be, for example but not limited to, an electronic, magnetic, optical, electromagnetic, infrared, or semiconductor system, apparatus, device, or propagation medium. More specific examples (a non-exhaustive list) of the computer-readable medium include an electrical connection having one or more wires, a portable computer diskette, a random access memory (RAM), a read-only memory (ROM), an erasable programmable read-only memory (EPROM), an electrically erasable programmable read-only memory (EEPROM), or Flash memory, an optical fiber, and a portable compact disc read-only memory (CDROM). Note that the computer-readable medium can even be paper or another suitable medium upon which a program is printed, as the program can be electronically captured, via for instance, optical scanning of the paper or other medium, then compiled, interpreted or otherwise processed in a suitable manner as necessary, and then stored in a computer memory.

Figure 2:
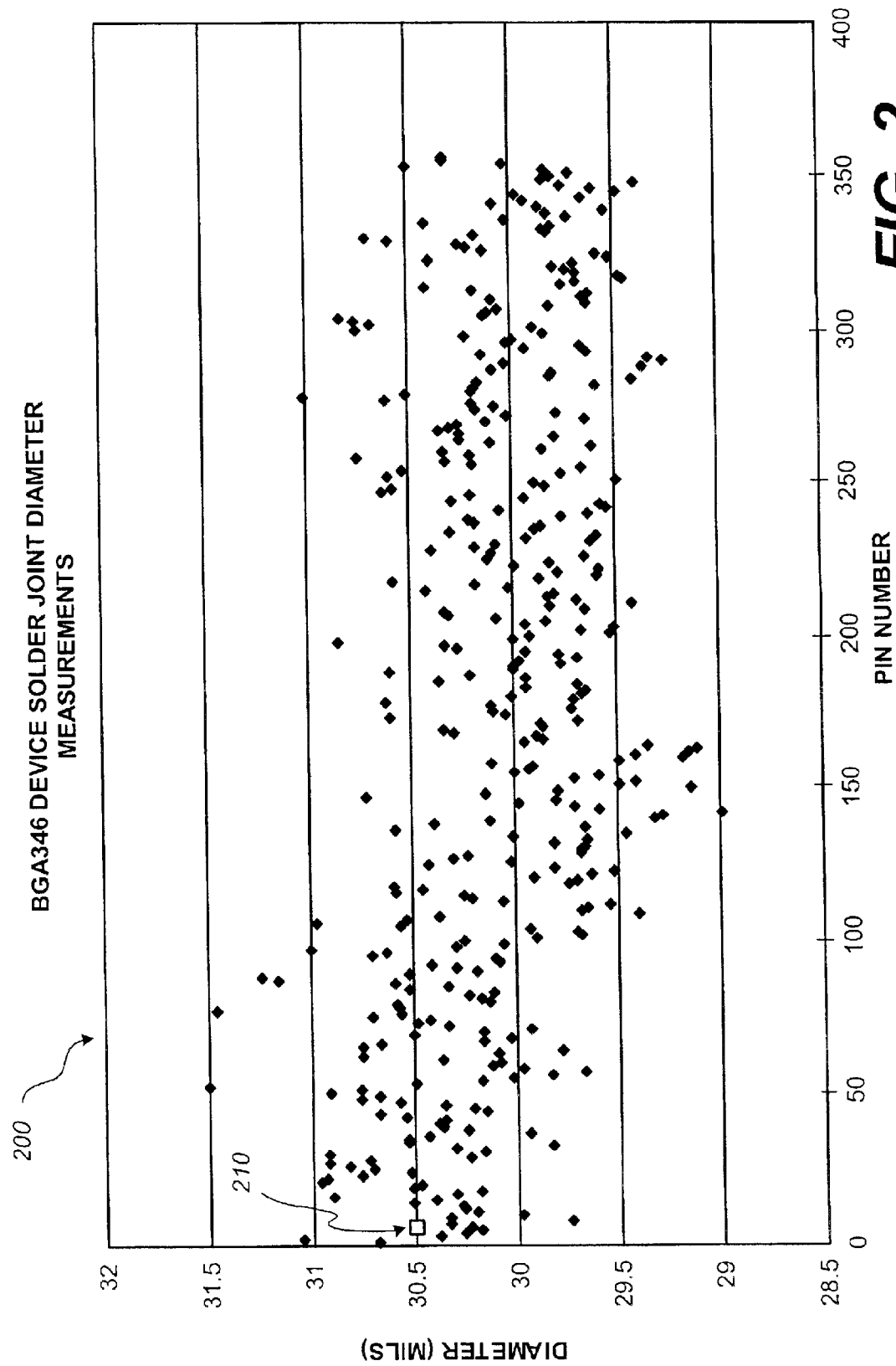
FIG. 2 is a plot of solder joint diameter values for an exemplar ball-grid array device.

FIG. 2 illustrates a plot 200 of sample data points measured and recorded from a particular type of BGA device package. As illustrated in the plot of FIG. 2, the data includes the diameter in mils. for more than 350 solder joints inspected. One of the solder joints associated with a pin near the left of the plot, identified by reference number 210, has a known defect. As illustrated solder joint 210 has a diameter of approximately 30.5 mils and is nearly in the middle of the range of recorded diameters for the BGA package. More specifically, the recorded diameters for individual solder joints range from 29 mils. to 31.5 mils. for a total variation in diameter of 2.5 mils. Clearly this view of the data indicates that it is impossible to set either a low or a high threshold that would isolate and/or otherwise identify the known solder joint with the defect from a host of acceptable solder joints. Consequently, an acceptable solution is not available for setting pass/fail thresholds given this data arrangement.

Figure 3:
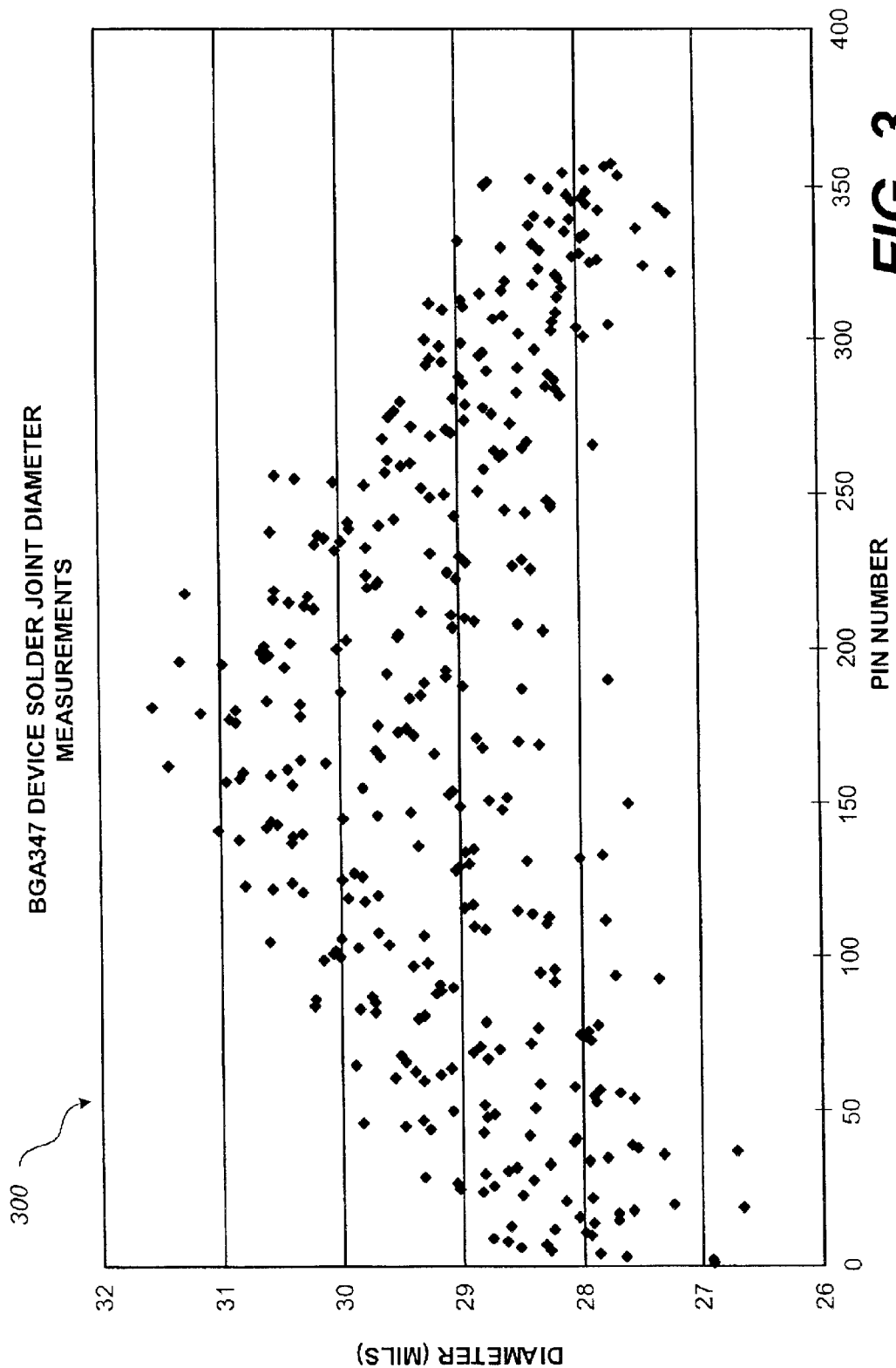
FIG. 3 is a plot of solder joint diameter values for another exemplar ball-grid array device.

Similarly, FIG. 3 illustrates a plot 300 of sample data points measured and recorded from another BGA device package type. As illustrated in the plot of FIG. 3, the data includes the diameter in mils. for more than 350 solder joints inspected. Here, none of the solder joints is defective. The recorded diameters for individual solder joints range from approximately 26.75 mils. to 31.5 mils, a range of 4.75 mils. or nearly twice the range of diameters recorded for solder joints associated with the BGA device represented in FIG. 2. Importantly, despite the dramatic increase in the range of solder joint diameters recorded, not a single solder joint in plot 300 is defective, further illustrating that a direct application of pass/fail thresholds based solely on individual solder joint diameter measurements may lead to inaccurate defect calls.

Figure 4:
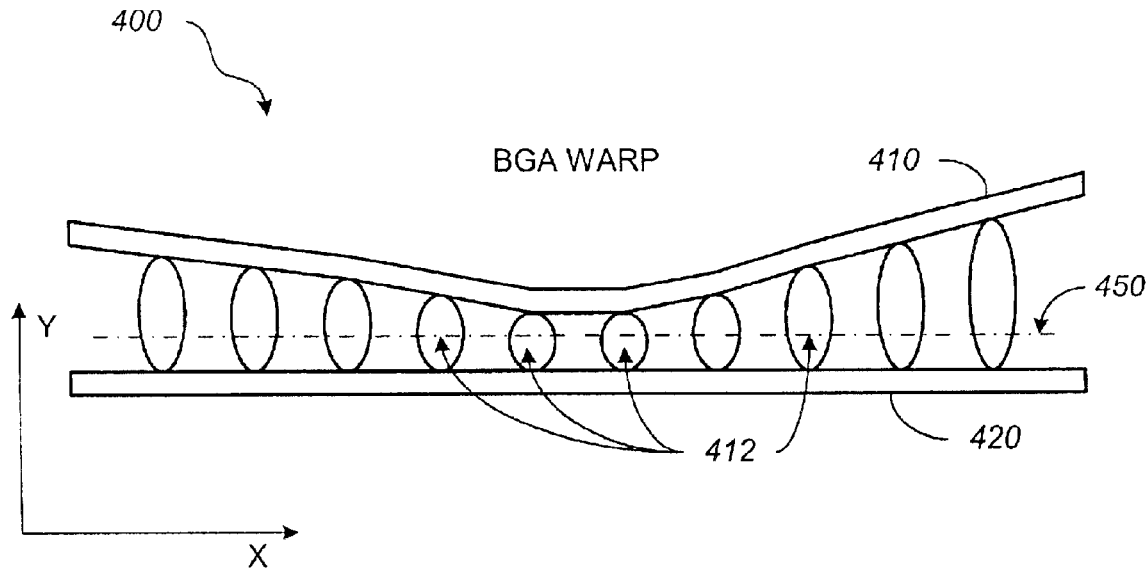
FIG. 4 is a side-view illustrating the effect of ball-grid array warp on individual solder joint diameters.

Reference is now directed to the side view of FIG. 4. As illustrated in FIG. 4, a printed-circuit assembly 400 may comprise a BGA device 410 and a printed-circuit board 420 electrically and physically connected at a plurality of substantially aligned points via a plurality of solder joints 412. It is important to note that the illustration is not to scale. The relative height (i.e., the thickness) of the BGA device 410 and the printed-circuit board 420 used in forming the printed-circuit assembly 400 will often vary and the size of the various solder joints formed by the plurality of solder balls will generally be significantly smaller.

As further illustrated in the side view of FIG. 4, the BGA device 410 may warp with an upward curve such that opposing ends of the BGA device 410 are "pulled" away from the mounting (i.e., the upper) surface of the printed-circuit board 420. The BGA device 410 may warp due to thermal expansion mismatches within the package and/or for other reasons such as stress applied by the printed-circuit board. The solder joints 412 cool before the materials in the BGA device 410, thus setting the warp. Because the volume of material (solder) in each of the solder balls remains fixed, those connection points with mounting surfaces (the underside of the BGA device 410 and the upper surface of the printed-circuit board 420) further removed from each other in the "Z" dimension will have a reduced diameter when measured at the focal plane 450. As previously explained, this BGA device warp can cause a wide variation in the measured diameters of solder joints 412. Because of the upward curvature of the BGA device 410, solder joints near the center of the BGA device 410 typically have a larger diameter than solder joints toward the outer edges of the BGA device 410.

Figure 5:
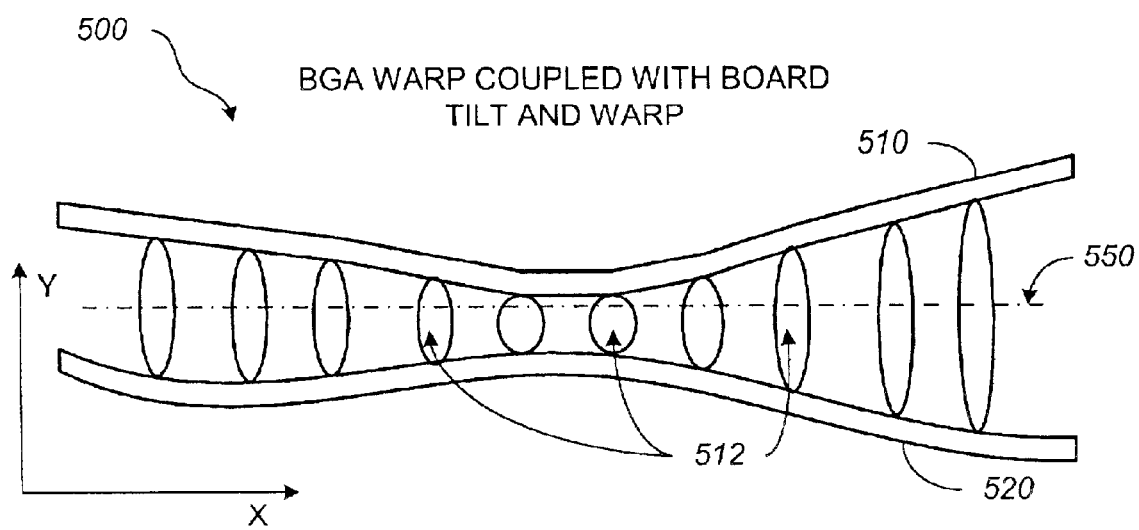
FIG. 5 is a side-view illustrating the effect of ball-grid array warp coupled with printed-circuit board tilt and warp on individual solder joint diameters.

As illustrated in the side view of FIG. 5, a printed-circuit assembly 500 may comprise a BGA device 510 and a printed-circuit board 520 electrically and physically connected at a plurality of substantially aligned points via a plurality of solder joints 512. As with the illustration of FIG. 4, the printed-circuit assembly 500 of FIG. 5 is not to scale. As illustrated in the side view of FIG. 5, there are at least two other factors that can result in an acceptable variance in solder joints measurements for solder joints associated with a BGA device 510: printed-circuit board warp and BGA device tilt. A BGA device tilts when one corner or more corners is at a different "Z" value than the remaining corners of the BGA device 510. As in the case of BGA device warp as shown in FIG. 4, printed-circuit board warp may be non-linear and vary across both the X and Y (i.e., into the page) dimensions. Consequently, the connection points with mounting surfaces (the underside of the BGA device 510 and the upper surface of the printed-circuit board 520) further removed from each other in the "Z" dimension, will have a reduced diameter when measured at the focal plane 550. As previously explained, the resulting wide variation in the measured diameters of solder joints 512 makes it difficult to use this information as the sole indicator of where to place pass/fail criteria for use in the solder-joint inspection system 100 (FIG. 1).

Figure 6:
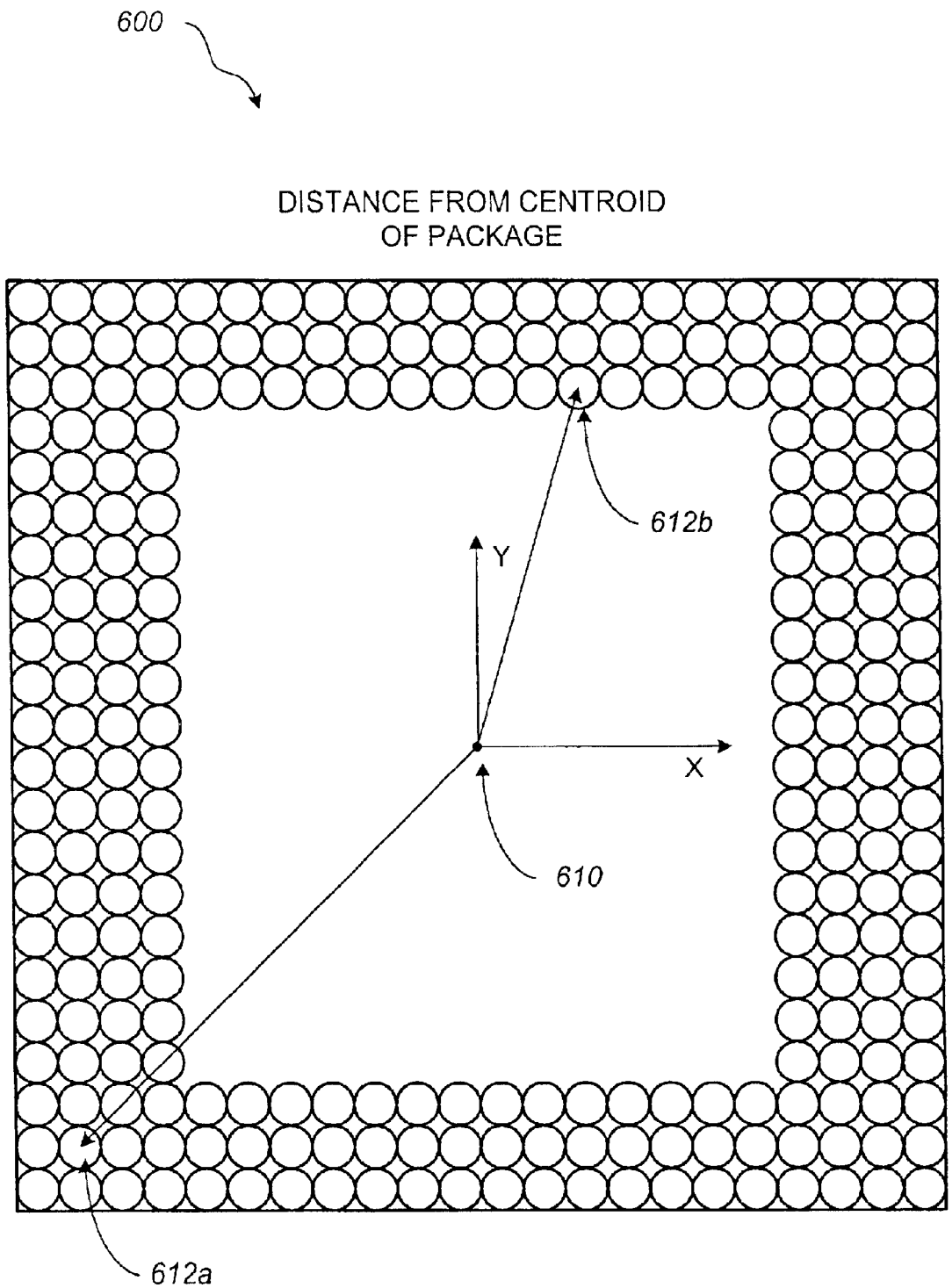
FIG. 6 is a plan-view of an exemplar ball-grid array device illustrating a method for determining the distance from a centroid of a device for two solder joints.

Reference is now directed to the plan view of FIG. 6, which illustrates a method for associating the distance from the centroid 610 of an exemplar BGA device 600 with each of the plurality of solder joints 612 located on the mounting surface of the device. As illustrated in FIG. 6, the solder-joint inspection system 100 can be used to identify a centroid 610 of a particular BGA device 600 presently under test. After having identified the centroid 610 of the BGA device 600 in the X-Y plane, the solder-joint inspection system 100 can be used to determine and store the distance of the center of each respective solder joint 612 from the centroid 610.

Figure 7:
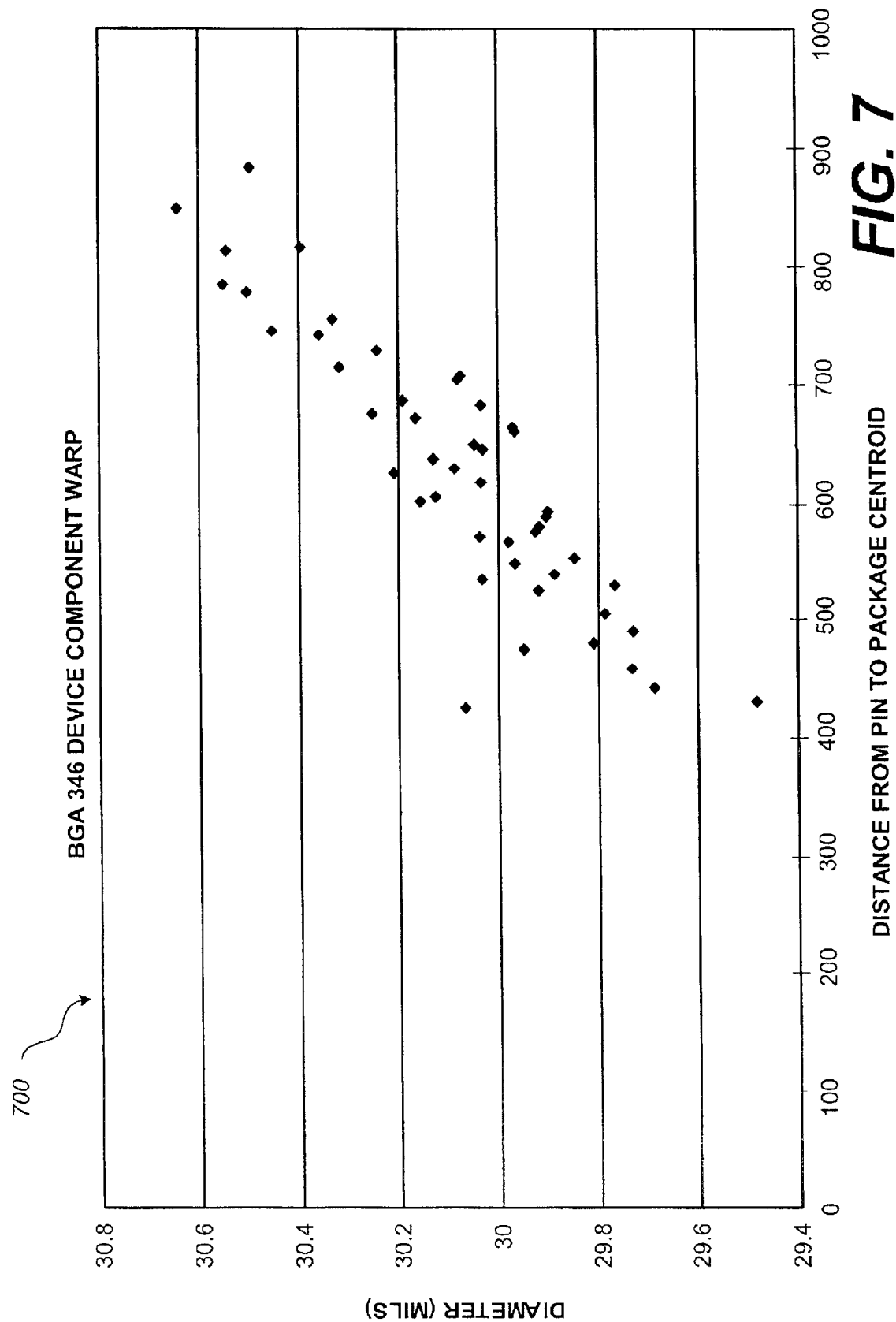
FIG. 7 is an exemplar plot of solder joint diameter values versus solder joint (pin) distance from a package centroid.
Figure 8:
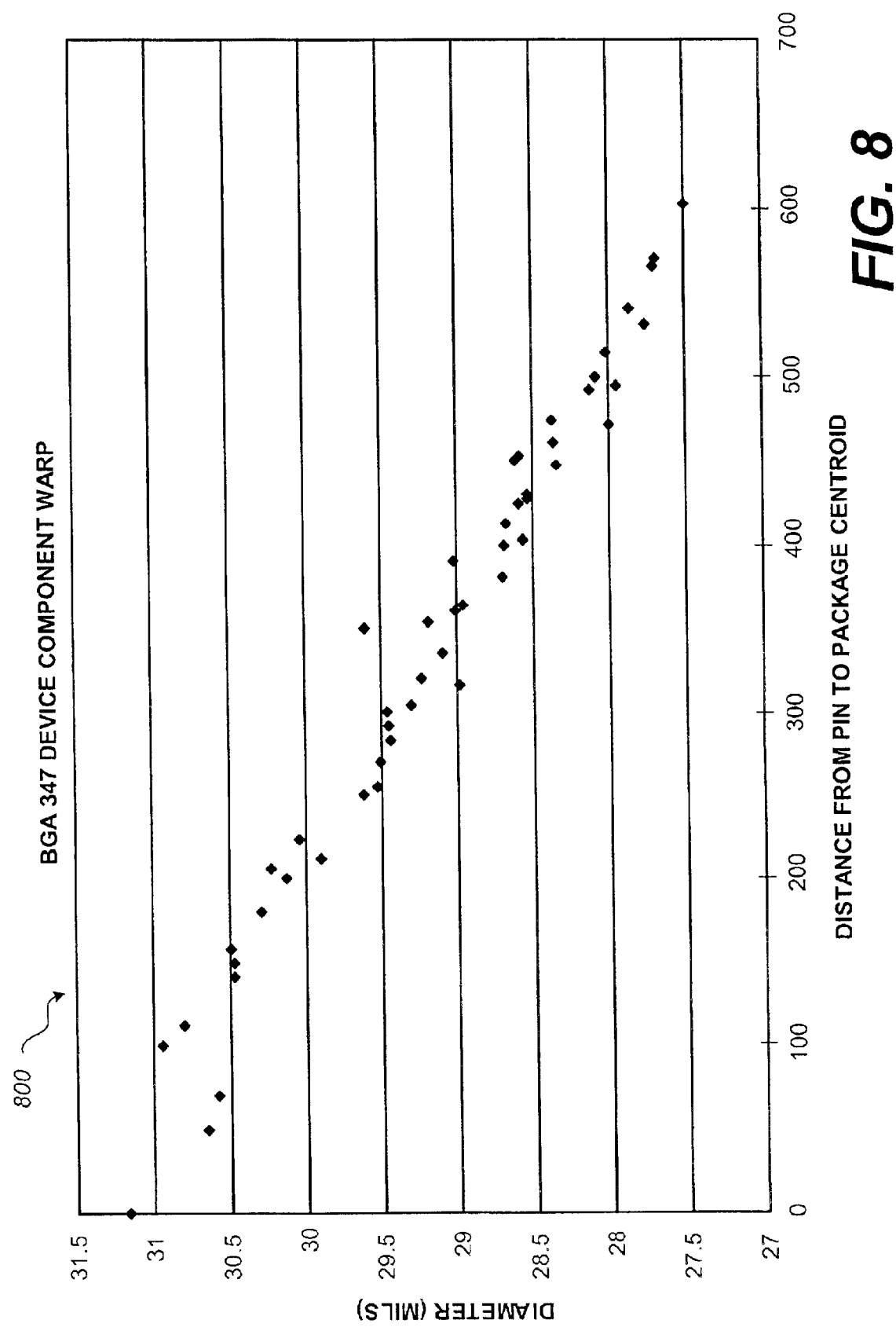
FIG. 8 is a second exemplar plot of solder joint diameter values versus solder joint (pin) distance form a package centroid.

The significance of these distance measurements will be appreciated when observing the sample data plots of FIGS. 7 and 8. The data plot 700, illustrated in FIG. 7, arranges the solder joint diameters for the various conducting points of the exemplar BGA device type by their distance from the centroid 610 of the BGA device 600 (FIG. 6). As opposed to the sample data plot of FIG. 2, the data indicates a somewhat linear relationship between solder joint diameter in mils. and the distance of the solder joint from the centroid 610.

Similarly, the data plot 800, illustrated in FIG. 8, arranges the solder joint diameters for the various conducting points of the exemplar BGA device type by their distance from the centroid of the BGA device. As opposed to the sample data plot of FIG. 3, and as in the case of the sample data plot 700 of FIG. 7, the data indicates a somewhat linear relationship between solder joint diameter in mils. and the distance of the solder joint from the centroid. However, in the case of the BGA package type analyzed and plotted in FIG. 8, the slope of the linear relationship is negative with respect to an increase in distance of the respective solder joint from the centroid of the device. Clearly these views indicate that it is possible to configure one or more thresholds for each separate solder joint of a BGA device when the thresholds account for the acceptable variance that can be expected across the various solder joints arranged along the X-Y plane.

For example, an upper pass/fail threshold for solder joint diameter may mirror the average diameter vs. distance from the centroid for solder joints associated with a particular printed-circuit device. The upper pass/fail threshold may be applied in a linear fashion having a fixed positive delta from the average diameter vs. distance measurements recorded for the particular printed-circuit device. Actual solder-joint diameters that exceed the upper pass/fail threshold where the distance between the mounting surfaces is not relatively close may be considered as having excess solder and may be marked for further investigation.

Similarly, a lower pass/fail threshold may mirror the diameter vs. distance from the centroid for the solder joints on the printed-circuit device with the lower pass/fail threshold having a fixed negative delta from the diameter vs. distance measurements recorded for the printed-circuit device. Actual solder-joint diameters that exceed the lower pass/fail threshold may be indicative of an open circuit condition and may be marked for further observation.

Figure 9:
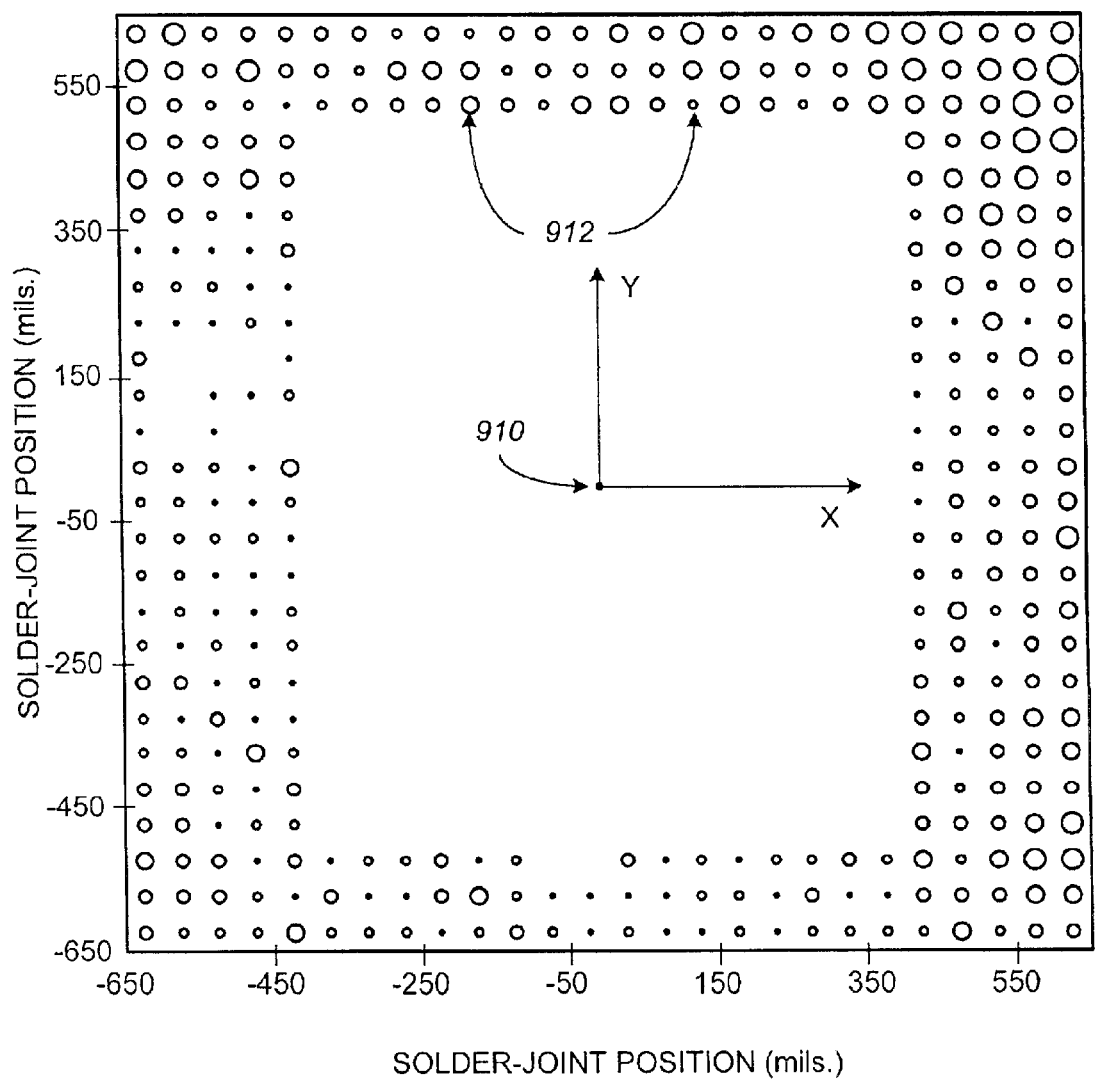
FIG. 9 is an exaggerated plan-view of solder joint diameters for a first arrangement of solder joints on an exemplar ball-grid array package.
Figure 10:
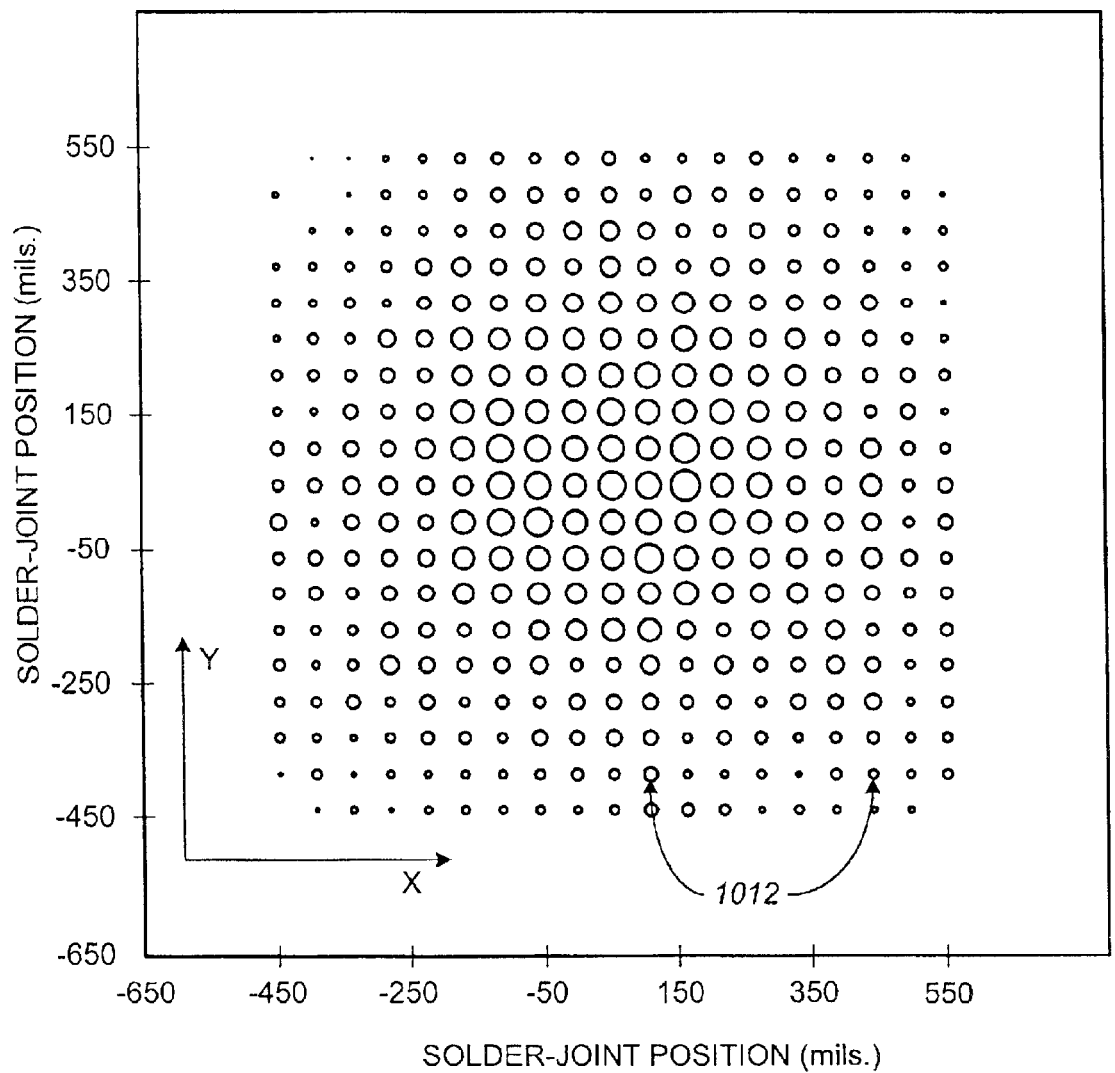
FIG. 10 is an exaggerated plan-view of solder joint diameters for a second arrangement of solder joints on an exemplar ball-grid array package.

FIGS. 9 and 10 present plan views of two exemplar BGA devices. The BGA device 900 illustrated in FIG. 9 is representative of an arrangement that places solder joints in rows and columns near the external edges of the device. As illustrated in the plan view of FIG. 9, the mounting surface of the BGA device 900 is substantially coplanar with the X and Y dimensions of the solder-joint inspection system 100

(FIG. 1). For purposes of illustration, the exaggerated diameter chart reveals a number of solder joints 912 across the mounting surface. The diameter of each of the individual solder joints shown is substantially out of scale in order to illustrate solder-joint diameter variance across the individual solder joints on the BGA device 900. As shown in the plan view of FIG. 9, the BGA device 900 reveals a non-linear "Z" dimension variation in the diameters of each of the solder joints 912. Here, the solder joint diameter variance is somewhat random across the mounting surface of the BGA device 900.

The BGA device 1000 illustrated in FIG. 10 is representative of an arrangement that places solder joints 1012 in rows and columns centered about the centroid of the mounting surface of the device. As illustrated in the plan view of FIG. 10, the mounting surface of the BGA device 1000 is also substantially coplanar with the X and Y dimensions of the solder-joint inspection system 100 (FIG. 1). As with the exaggerated solder-joint diameter chart of FIG. 9, the exaggerated solder-joint diameter chart of FIG. 10 reveals a number of solder joints 1012 across the mounting surface. As shown in the plan view of FIG. 10, the BGA device 1000 has warped in the typical manner, with the solder joints closest to the external edges having the smallest diameters and those solder joints relatively close to the centroid of the BGA device 1000 having the largest diameters.

Figure 11:
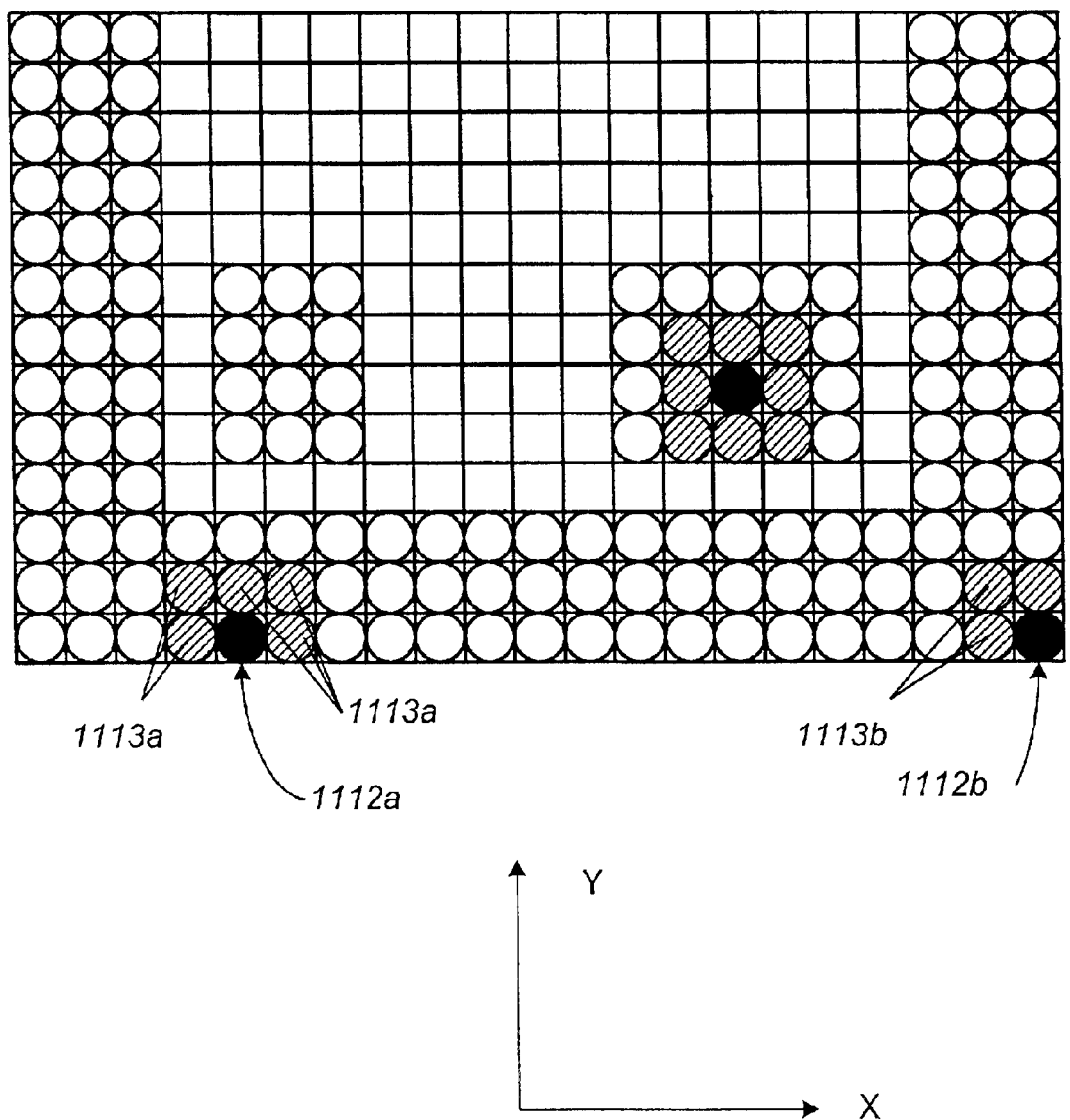
FIG. 11 is a schematic illustrating the association of identified solder joints on an exemplar ball-grid array package with its neighboring solder joints that may be applied by the circuit inspection system of FIG. 1.

In accordance with preferred embodiments of the improved solder-joint inspection system 100 (FIG. 1) and the associated method for adapting test thresholds, a near neighbor analysis is performed for each of the solder joints associated with a printed-circuit device (e.g., BGA device 900) in order to account for the acceptable measurement variance across the solder joints of the respective printed-circuit device. The technique assumes that there is change in solder joint measurements over the package, but that measurement changes from one solder joint to adjacent solder joints should be very small. Each solder joint associated with a BGA device may be associated with a set of near neighbor solder joints as illustrated in the partial plan view of FIG. 11. When a solder joint is located along the edge of the BGA device 1100 as is the case with solder joint 1112a, the five adjacent solder joints 1113a will form the elements of the near neighbor set for solder joint 1112a. For a solder joint located in a corner of the array of solder joints, as is the case with solder joint 1112b, the three adjacent solder joints 1113b will form the elements of the near neighbor set for solder joint 1112b. As further illustrated, a "field" solder joint (i.e., a solder joint surrounded by eight adjacent solder joints) may be associated with the eight adjacent solder joints. Note that a number of different methods could be used to choose neighbor pins (i.e., solder joints) in addition to those illustrated in FIG. 11. For example, solder joints within a specified number of rows or columns could be considered among various other methods for associating neighbor solder joints with a solder joint under test.

A number of different methods may be used to estimate an appropriate solder joint measurement from the same measurement recorded for the solder joints in a particular solder joints near neighbor set. For example, the measured values associated with each of the solder joints within a near neighbor set can be statistically analyzed to set an expected measurement for an identified solder joint. In this regard, the mean, median, or average measured value for the set of measurements can be used as the expected value the identified solder joint. In some arrangements, an estimated value may be predicted based on a measured characteristic. For example, the height of a solder joint could be measured and knowing the volume of an original solder ball an estimate of an expected diameter for the associated solder joint may be determined.

A near neighbor error value can then be calculated for each of the plurality of solder joints by comparing the actual solder joint measurement with the expected value derived for the solder joint from the measurements of the near neighbor set. The near neighbor error data for the exemplar BGA device types previously described is illustrated in the data plot of FIG. 12. In this regard, the data plot 1200 illustrates the relationship between the near neighbor error and pin (i.e., solder joint) sorted by BGA device type and error magnitude. As shown by the composite data plot 1200, the error signature of the exemplar BGA346 device is significantly different from the error signature of the BGA347 device.

Figure 12:
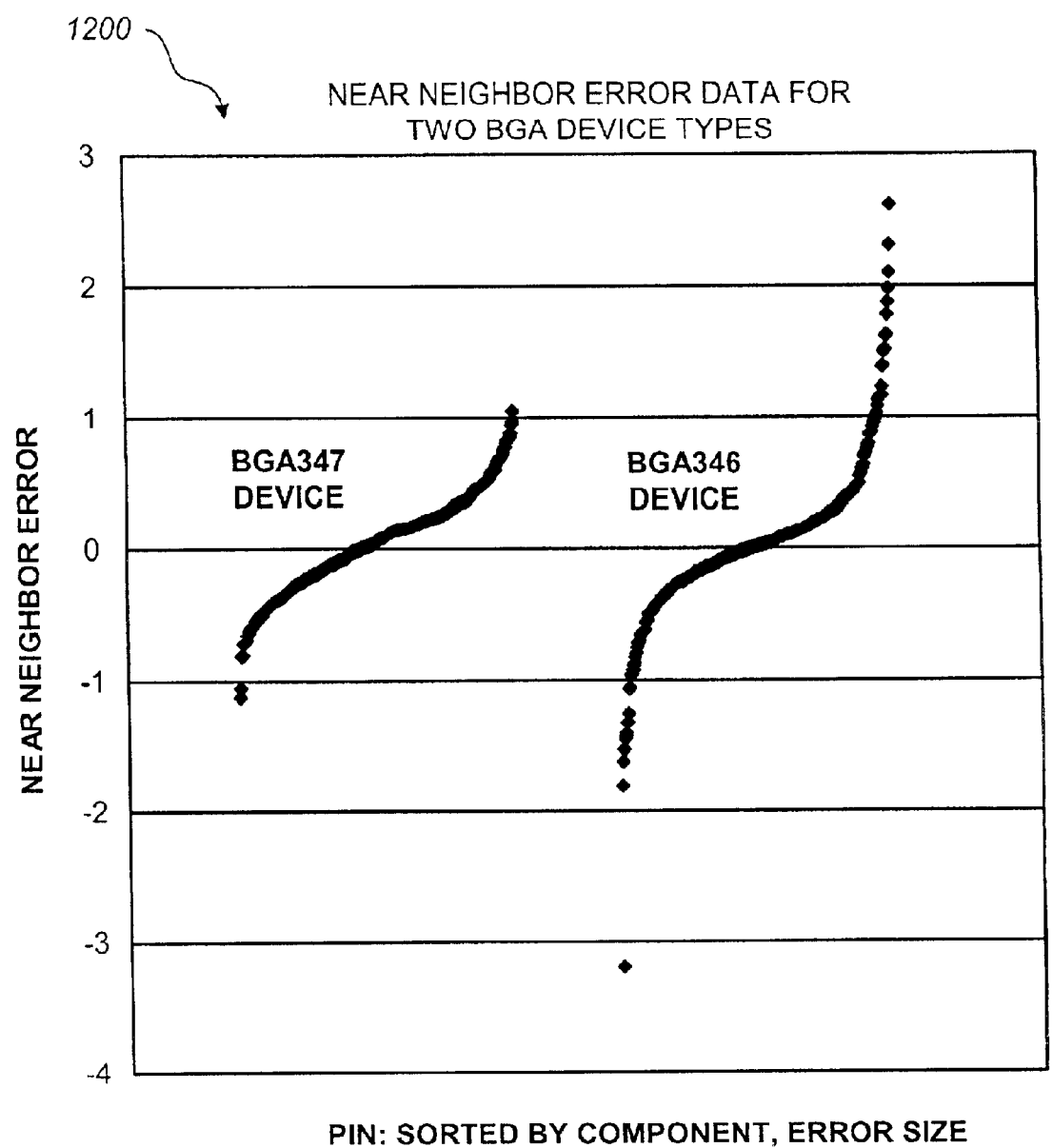
FIG. 12 is a plot of near neighbor solder joint diameter errors sorted by package type and error size that may be created by dated recorded by the circuit inspection system of FIG. 1.
Figure 13:
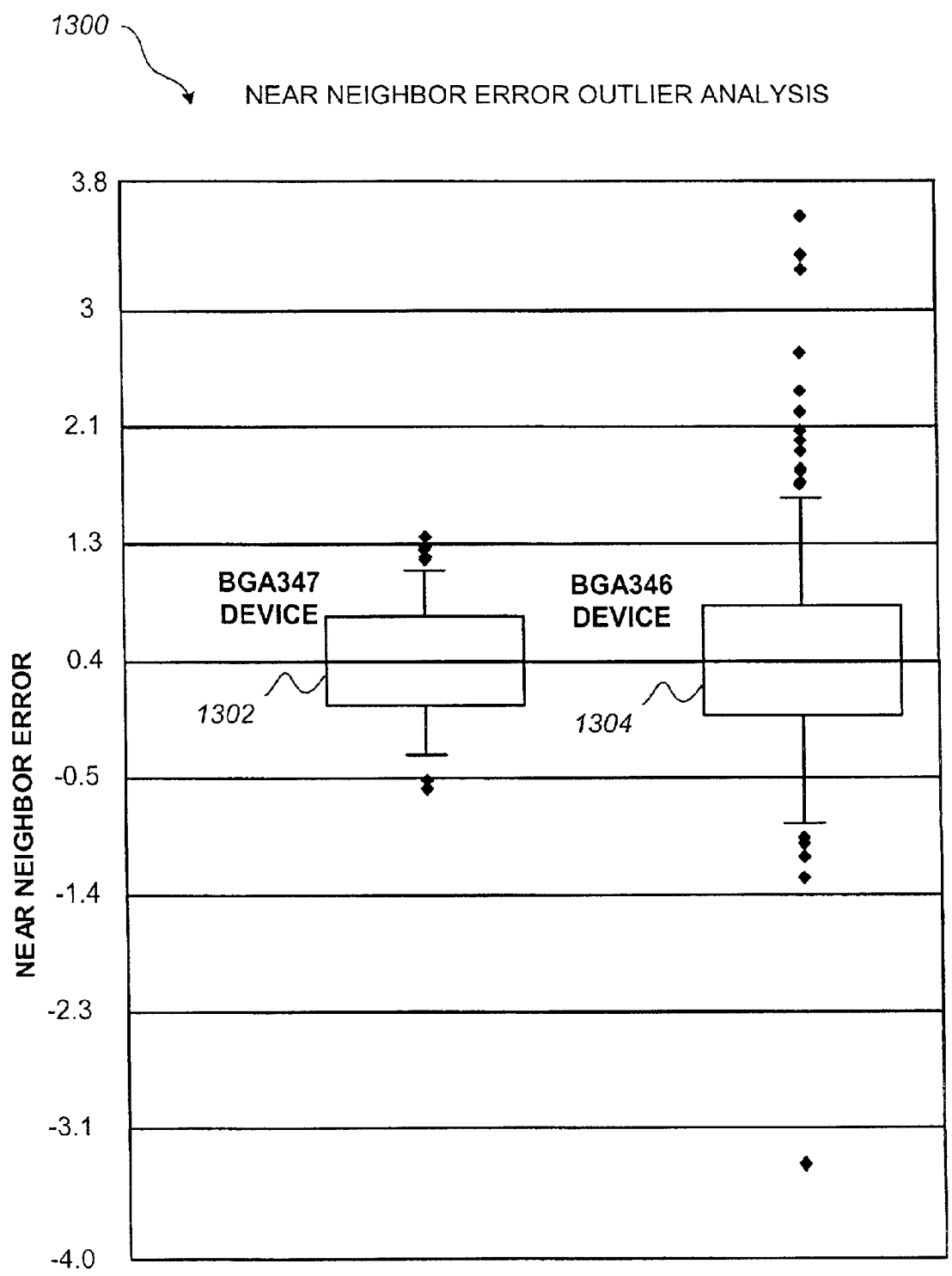
FIG. 13 is a plot illustrating a near neighbor solder-joint diameter errors outlier analysis that may be applied by the circuit inspection system of FIG. 1.

Reference is now directed to the near neighbor error outlier analysis plot illustrated in FIG. 13. The composite data plot 1300 illustrates a box plot analysis of the near neighbor error data plot 1200 (FIG. 12). A box plot is an effective visual representation of both central tendency and dispersion. It simultaneously shows the 25th, 50th (median), and 75th percentile scores, along with the minimum and maximum scores. The "box" of the box plot shows the middle or "most typical" 50% of the values, while the "whiskers" of the box plot show the more extreme values. The height of the boxes 1302 and 1304 for the respective BGA devices is representative of the interquartile range (IQR).

It has been discovered that considering any diameter error more than three times the IQR beyond the top of the respective box 1302, 1304 is an effective pass/fail threshold for BGA solder joints. As illustrated by the box plot data in the composite plot of FIG. 13, no outlier near neighbor error value for the BGA347 device type exceeds the contemplated (3 times IQR) value. In this case, the improved solder-joint inspection system 100 has accurately reported no defects associated with the solder joints of the exemplar BGA347 device. As further illustrated in the composite box plot 1300, the same cannot be said for the solder joint error outliers associated with the exemplar BGA346 device. As illustrated, several near neighbor error values exceed the contemplated error value threshold. As in the case of the other BGA device type, the improved solder-joint inspection method and associated method for adapting test thresholds has accurately identified that the exemplar BGA346 device has solder joint defects. As described above, this technique for adapting test thresholds compensates for BGA device warp, printed-circuit board warp, and BGA device tilt. The technique accurately identifies many BGA device solder joint open conditions that were previously undetected with the 5DX solder-joint inspection system.

Figure 14:
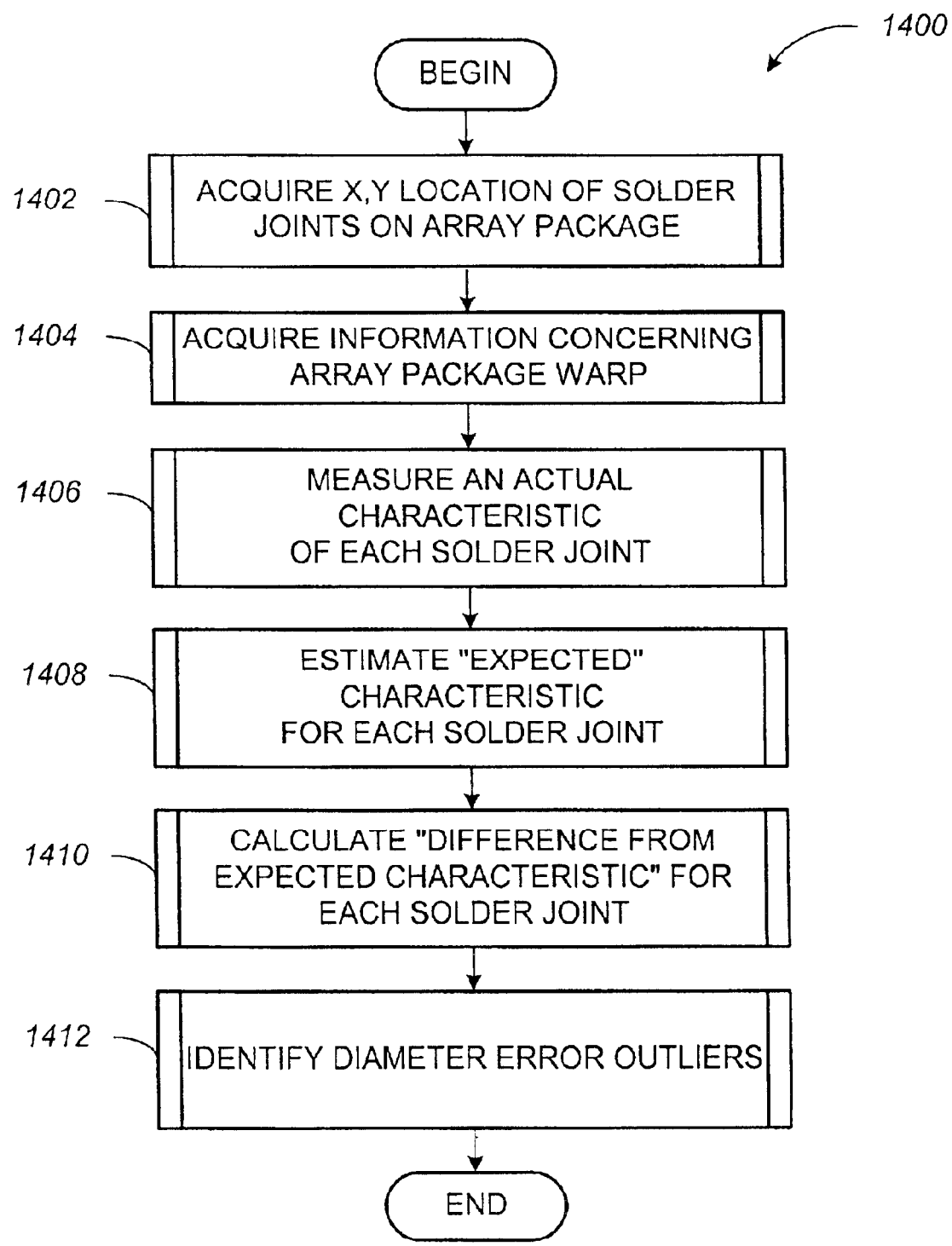
FIG. 14 is a flow diagram that illustrates a method for adapting test thresholds that may be practiced by the circuit inspection system of FIG. 1.

Reference is now directed to the flowchart of FIG. 14, which illustrates a method for identifying solder joint defects 1400 that may be practiced by the improved solder-joint inspection system 100 of FIG. 1. In this regard, the improved solder-joint inspection system 100 may begin practicing the method 1400 by acquiring the location of the conductive pins (i.e., the center of the array package solder joints) across the mounting surface of an array package device as indicated in step 1402. After having located each of the pins and thus the solder joints, the improved solder-joint inspection system 100 may acquire information concerning array package warp as illustrated in step 1404. This information may be measured using a laser rangefinder and/or by other methods such as but not limited to identifying the near neighbor conductor pins or solder joints for each solder joint on a device under test and estimating the package warp by observing one or more characteristics of the solder joints associated with the near neighbor pins. The improved solder-joint inspection system 100 may then measure and record the actual diameter and/or some other relational characteristic (i.e., the thickness, heel height, solder volume, etc.) of each solder joint as indicated in step 1406.

Thereafter, as illustrated in step 1408, the improved solder-joint inspection system may formulate an estimated or expected value for each of the solder joints. A number of different methods may be used by the solder-joint inspection system to derive the expected values. For example, measured diameters or some other characteristic of the solder joints along a row of solder joints in the X-dimension and/or along a column of solder joint diameters in the Y-dimension may be used to formulate a best fit polynomial equation for the corresponding data set formed by the measured diameters. The resulting best-fit polynomial equation may then be used to generate an expected value for each solder joint. In other embodiments, an expected value for each individual solder joint can be determined as a mathematical result from an expected best-fit result in the X-dimension in combination with a best-fit result in the Y-dimension.

Alternatively, a Fourier analysis can be applied to the measured data to generate an expected value for each of the solder joints. As is known, a Fourier transform presents a representation of a two-dimensional relationship as a weighted sum of sines and cosines. A forward transform goes from the spatial domain, which may be continuous or discrete, to the frequency domain, which is always continuous. Thus a Fourier transform can be used to analyze data in the frequency domain for high frequency changes in the measured diameters. As is known, high-frequency changes can be removed via a suitably configured filter. The inverse Fourier transform may then be applied to the data to derive the expected values for each of the solder joints. Irrespective of the method used to generate the expected values, the low-frequency (acceptable) variation in measured values across the array package device are reflected in the expected values and thus the modified pass/fail thresholds.

Next, as shown in step 1410, the improved solder-joint inspection system 100 may be programmed to compare the estimated or expected value generated in step 1408 with the respective measured value for each of the solder joints recorded in step 1406 to generate an error value. As described above, and as illustrated in step 1412, the improved solder-joint inspection system 100 may be programmed to store and analyze the errors for outliers. These outliers are indicative of unexpected (e.g., a high-frequency) variance in the solder joint measurement, which has been determined to be an accurate indicator of defective solder joints for BGA devices. It should be appreciated that the process steps illustrated in the flowchart of FIG. 14 may be repeated as desired to complete a solder joint analysis of other printed-circuit devices mounted on a printed-circuit assembly.

Figure 15:
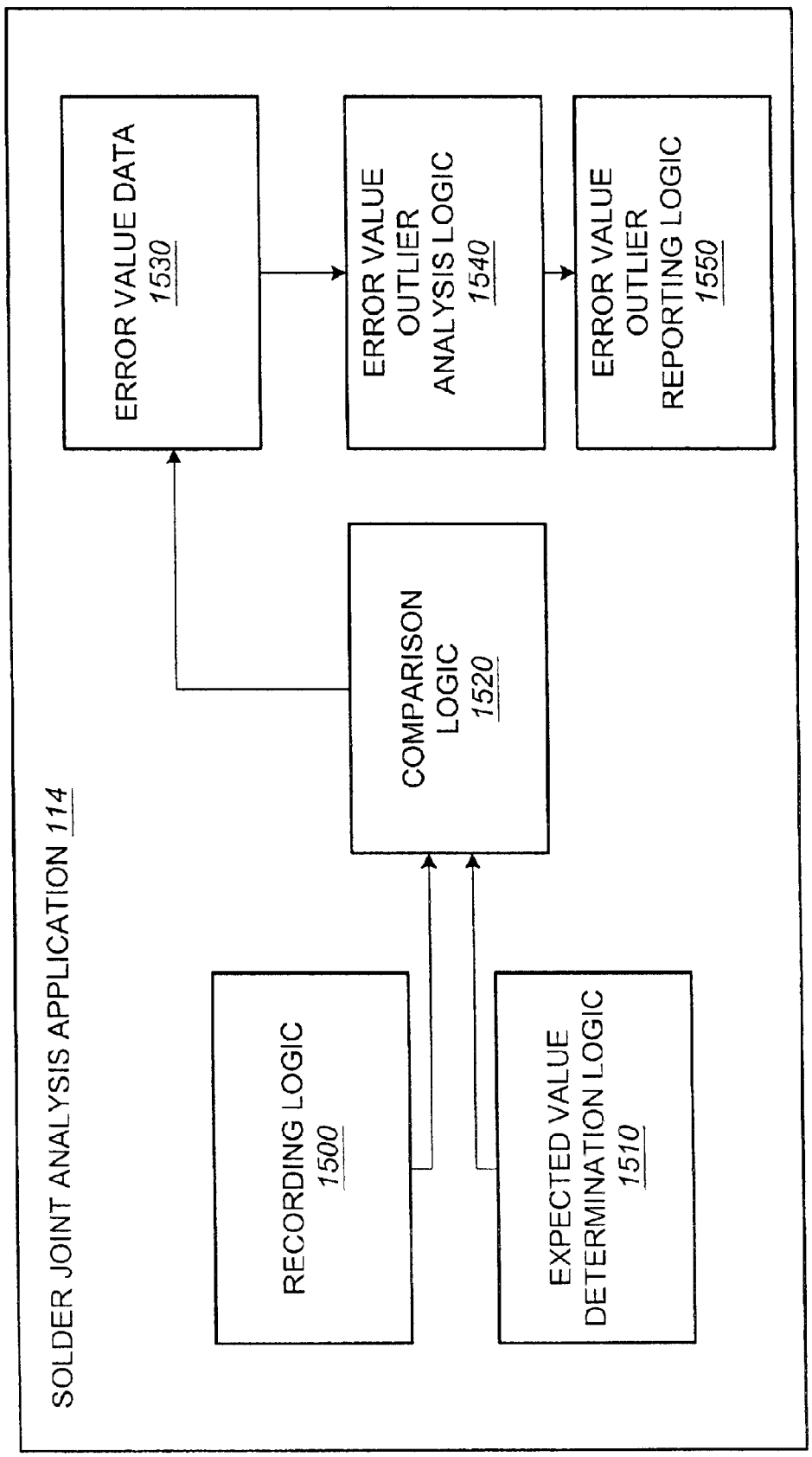
FIG. 15 is a functional block diagram illustrating various exemplar components of the solder joint analysis application of FIG. 1.

FIG. 15 is a functional block diagram illustrating various exemplar components of the solder-joint analysis application 114 of FIG. 1. In this regard the solder-joint analysis application 114 may include recording logic 1500 configured to receive one or more characteristic values observed in various images generated and analyzed by the solder-joint inspection system 100. The solder-joint analysis application 114 may also include logic 1510 configured to determine an expected value for each of the solder joints under observation. As previously described, the logic 1510 may use any of a number of methods for generating an expected measurement value for each respective solder joint that accounts for variance between the mounting surfaces of an associated device and the printed-circuit board.

As shown in FIG. 15, both the recording logic 1500 and the logic 1510 may be configured to provide information regarding each respective solder joint to comparison logic 1520. In turn, comparison logic 1520 may be configured to determine the difference in magnitude between the measured (i.e., the recorded measurement value) and the associated expected value for each of the respective solder joints under observation. As further illustrated in the block diagram, the comparison logic 1520 may be configured to forward each of the respective error data values to an error value data array 1530.

Next, the error-value outlier-analysis logic 1540 may be configured to receive a plurality of the respective error data values and perform an outlier analysis on the information. After having identified the error value outliers in the outlier analysis logic 1540, the solder joint analysis application 114, may forward identification information associated with the outlier data values that exceed a threshold to the outlier error reporting logic 1550. The outlier error reporting logic 1550, may in turn provide position and/or other identifiers for the associated solder joints to one or more peripheral devices in communication with the solder-joint inspection system 100.

Figure 16:
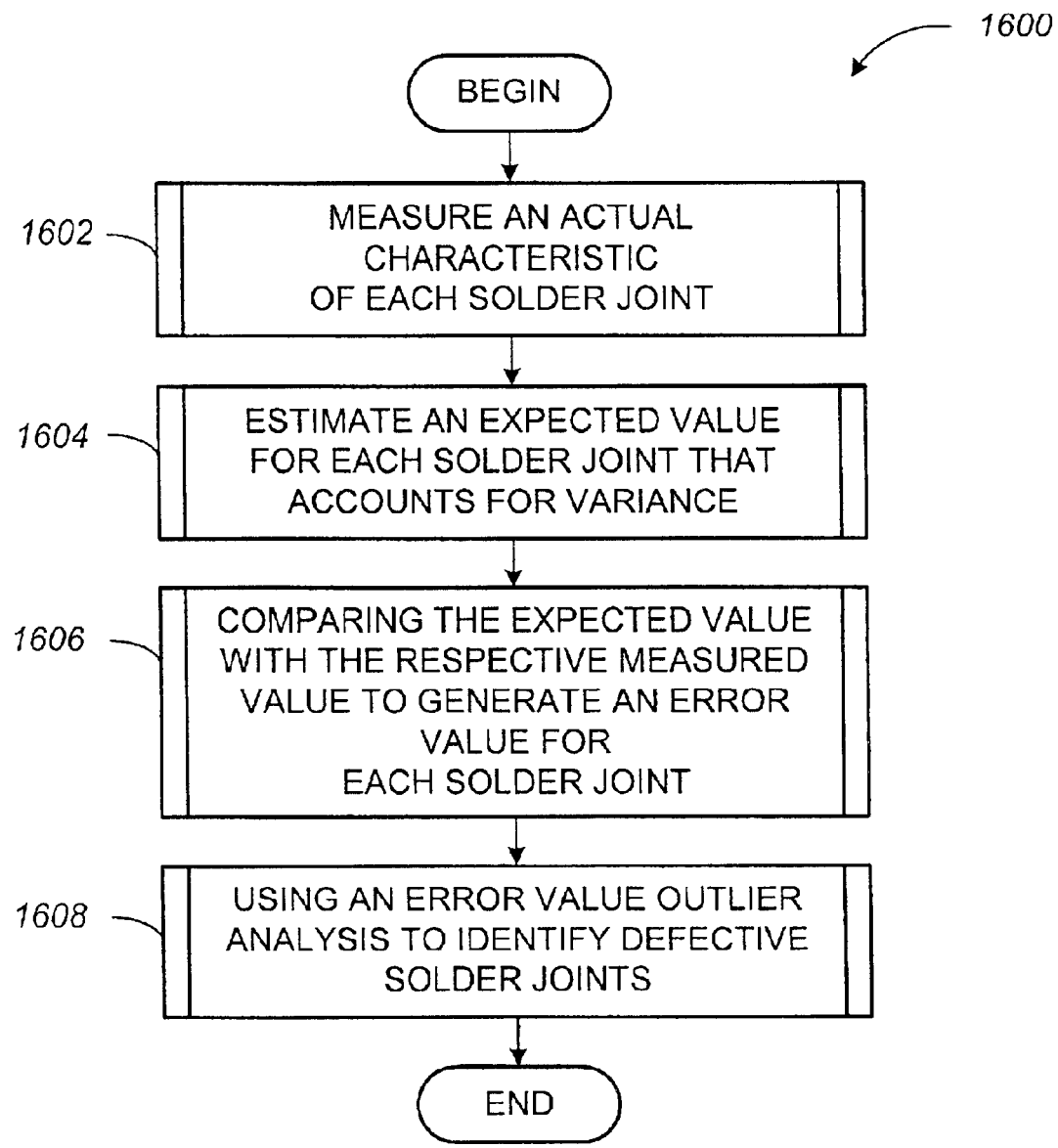
FIG. 16 is a flow diagram that illustrates a method for identifying solder-joint defects that may be practiced by the circuit inspection system of FIG. 1.

FIG. 16 is a flow diagram that illustrates a method for identifying solder-joint defects 1600 that may be practiced by the circuit inspection system of FIG. 1. In this regard, the improved solder-joint inspection system 100 may begin practicing the method 1600 by measuring and recording a physical characteristic of each solder joint associated with a particular array package. After having measured each of the solder joints, the improved solder-joint inspection system 100 may use information concerning array package warp and/or printed circuit board warp to estimate an expected value for each of the measured solder joints as indicated in step 1604.

Next, as illustrated in step 1606, the improved solder-joint inspection system 100 may be configured to compare the expected value with the respective measured value to generate an error value for each solder joint under observation. As indicated in step 1608, the plurality of error values generated in step 1606, may be applied in an error data value outlier analysis to identify defective joints.

While particular embodiments of the improved solder-joint inspection system 100 have been disclosed in detail in the foregoing description and drawings for purposes of example, it will be understood by those skilled in the art that variations and modifications thereof can be made without departing from the scope of the invention as set forth in the following claims. For instance, other solder-joint measurements associated with non-array package type devices can be expected to reflect low-frequency variation for various reasons including those described above which result in "Z"-dimension variance between the mounting surfaces. Consequently, one or more related techniques for adapting pass/fail thresholds for non-array package solder joints. The present disclosure is intended to include the application of these techniques.

Thus, having described the systems and methods for identifying solder joint defects, I claim the following:

1. A method for adapting test thresholds, comprising the following steps:
   acquiring location information for a plurality of solder joints on a printed-circuit device;

obtaining information indicative of the variation in distance between a mounting surface of the printed-circuit device and a printed-circuit board; recording a measurement of a physical property of a plurality of solder joints used to couple the printed-circuit device to the printed-circuit board;

analyzing recorded measurements of a set of neighbor solder joints to calculate a range of acceptable measurements for each respective neighbor solder joint responsive to variation in distance between the mounting surface of the printed-circuit device and the printed-circuit board, wherein analyzing is responsive to a best fit polynomial equation using the recorded measurements; and setting at least one threshold responsive to the range.

2. The method of claim 1, wherein the step of acquiring location information comprises an investigation of an array package.

3. The method of claim 1, wherein the step of recording comprises a diameter measurement.

4. The method of claim 1, wherein the step of recording comprises a height measurement.

5. The method of claim 1, wherein the step of recording comprises a volume measurement.

6. The method of claim 1, wherein analyzing comprises performing a statistical analysis.

7. The method of claim 6, wherein the statistical analysis comprises calculating the median of the recorded measurements of the identified set of neighbor solder joints.

8. The method of claim 6, wherein of statistical analysis is performed on a set of solder joints equidistant from the centroid of the printed-circuit device.

9. The method of claim 1, wherein estimating comprises applying the recorded measurements of a plurality of solder joints in a Fourier analysis.

10. The method of claim 9, wherein the Fourier analysis comprises the application of a high-frequency filter on the recorded measurements of an identified set of solder joints distributed across the surface of the device.

11. The method of claim 1, wherein setting further comprises:

comparing the expected value with the recorded measurement to generate an error value for the plurality of solder joints on the printed-circuit device; and performing an outlier analysis on the plurality of error values to establish at least one threshold value.

12. The method of claim 11, wherein comparing the expected value with the recorded measurement comprises a mathematical combination of the expected value with the recorded measurement.

13. The method of claim 12, wherein the mathematical combination comprises a difference.

14. The method of claim 1, wherein the step of obtaining comprises measuring the distance between a mounting surface of the printed-circuit device and a printed-circuit at a plurality of locations.

15. The method of claim 1, wherein the step of acquiring location information comprises an investigation of a quad flat pack package.

16. The method of claim 1, wherein the step of recording comprises a two-dimensional measurement.

17. The method of claim 1, wherein the step of recording comprises a three-dimensional measurement.

18. A method for identifying solder joint defects, comprising:

recording a measurement associated with a plurality of solder joints on a printed-circuit device;

analyzing the measurement associated with each of a set of neighboring solder joints to calculate an expected value for the measurement associated with each of the solder joints that accounts for acceptable variance in the distance between the mounting surfaces of a printed-circuit device and a printed-circuit board coupled by the solder joints, wherein analyzing is responsive to a best fit polynomial equation using the recorded measurements;

comparing the recorded measurement with the expected value for the plurality of solder joints to generate a respective error value; and identifying defective solder joints by applying an error value outlier analysis to the plurality of error values.

19. The method of claim 18, wherein recording comprises an investigation of an array package.

20. The method of claim 18, wherein recording comprises a diameter measurement.

21. The method of claim 18, wherein analyzing an expected value for the plurality of solder joints comprises performing a statistical analysis.

22. The method of claim 21, wherein the statistical analysis comprises calculating the median of the recorded measurements of the identified set of neighboring solder joints.

23. The method of claim 18, wherein estimating an expected value for the plurality of solder joints comprises performing a statistical analysis on the recorded measurements of a set of solder joints equidistant from the centroid of the printed-circuit device.

24. The method of claim 18, wherein estimating an expected value for the plurality of solder joints comprises applying the recorded measurements of a plurality of solder joints in a Fourier analysis.

25. The method of claim 24, wherein the Fourier analysis comprises the application of a high-frequency filter on the recorded measurements of a plurality of solder joints.

26. The method of claim 18, wherein comparing the expected value with the recorded measurement comprises a mathematical combination of the expected value with the respective recorded measurement.

27. The method of claim 26, wherein the mathematical combination comprises the difference of the expected value with the respective recorded measurement.

28. The method of claim 26, wherein identifying defective solder joints comprises a box plot analysis responsive to the plurality of error values.

29. The method of claim 18, wherein the step of recording comprises an investigation of a quad flat pack package.

30. The method of claim 18, wherein the step of recording comprises a one-dimensional measurement.

31. The method of claim 18, wherein the step of recording comprises a two-dimensional measurement.

32. The method of claim 18, wherein the step of recording comprises a three-dimensional measurement.

33. An improved solder-joint inspection system, comprising:

means for measuring at least one characteristic of a plurality of solder joints located within a select area of a printed-circuit device;

means for computing an expected value for the measured characteristic for each of the plurality of solder joints that varies as a function of distance between the mounting surface of the printed-circuit device and a printed-circuit board over the select area of the printed circuit device, wherein computing expected value is responsive to a best fit polynomial equation using the measurements; and means for formulating an error value as a function of the measured characteristic and the expected value for the plurality of solder joints.

34. The system of claim 33, further comprising:
means for analyzing the plurality of error values to identify solder joint defects.

35. The system of claim 34, wherein the means for analyzing comprises a box plot.

36. The system of claim 33, wherein the means for measuring comprises an automated X-ray inspection system.

37. The system of claim 33, wherein the means for measuring comprises an optical inspection system.

38. A solder-joint defect analysis detection program stored on a computer-readable medium, comprising:
logic configured to record at least one characteristic of a plurality of solder joints located within a select area of a printed-circuit device;
logic configured to determine an expected value for the at least one characteristic for the plurality of solder joints responsive to low frequency change in a solder joint characteristics across the device;
logic configured to generate an error value from a mathematical combination of the expected value and the recorded characteristic for the plurality of solder joints on the printed-circuit device; and
logic configured to identify error value outliers using a box plot analysis.

39. The program of claim 38, wherein the logic configured to record records at least one characteristic of a solder joint associated with an array package.

40. The program of claim 39, wherein the logic configured to determine an expected value is responsive to the distance between the mounting surface of a printed-circuit device and a printed-circuit board.

41. The program of claim 38, wherein the logic configured to determine an expected value reflects a statistical analysis of the recorded characteristic.

42. The program of claim 38, wherein the statistical analysis comprises calculating a median.

43. The program of claim 38, wherein the logic configured to generate an error value calculates the difference of the recorded characteristic and the expected value.

44. The program of claim 38, wherein the box plot analysis identifies error values that exceed a constant multiple of the interquartile range for the error values above a constant percentage of the error value data range.

* * * * *